US010246685B2

(12) United States Patent
Ishihara et al.

(10) Patent No.: US 10,246,685 B2
(45) Date of Patent: Apr. 2, 2019

(54) RECOMBINANT MDV1 AND THE USES THEREOF

(71) Applicant: Ceva Sante Animale, Libourne (FR)

(72) Inventors: Yukari Ishihara, Tokyo (JP); Motoyuki Esaki, Saitama (JP); Shuji Saitoh, Kanagawa (JP)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 15/547,737

(22) PCT Filed: Jan. 29, 2016

(86) PCT No.: PCT/EP2016/051871
§ 371 (c)(1),
(2) Date: Jul. 31, 2017

(87) PCT Pub. No.: WO2016/120421
PCT Pub. Date: Aug. 4, 2016

(65) Prior Publication Data
US 2018/0016559 A1    Jan. 18, 2018

(30) Foreign Application Priority Data

Jan. 29, 2015 (EP) .................................. 15305102

(51) Int. Cl.
| | |
|---|---|
| *C12N 15/869* | (2006.01) |
| *A61K 39/245* | (2006.01) |
| *C12N 7/00* | (2006.01) |
| *A61K 39/12* | (2006.01) |
| *A61K 39/17* | (2006.01) |
| *C12N 15/86* | (2006.01) |
| *A61K 39/00* | (2006.01) |

(52) U.S. Cl.
CPC ............... *C12N 7/00* (2013.01); *A61K 39/12* (2013.01); *A61K 39/17* (2013.01); *C12N 15/86* (2013.01); *A61K 2039/5256* (2013.01); *A61K 2039/552* (2013.01); *C12N 2710/16321* (2013.01); *C12N 2710/16343* (2013.01); *C12N 2710/16351* (2013.01); *C12N 2720/10034* (2013.01); *C12N 2720/10071* (2013.01); *C12N 2760/18134* (2013.01)

(58) Field of Classification Search
None
See application file for complete search history.

(56) References Cited

U.S. PATENT DOCUMENTS

| | | | | |
|---|---|---|---|---|
| 6,410,297 B1* | 6/2002 | Rong | ................... | A61K 39/255 424/229.1 |
| 2003/0157703 A1* | 8/2003 | Saitoh | ................. | C07K 14/005 435/320.1 |

FOREIGN PATENT DOCUMENTS

| | | |
|---|---|---|
| EP | 0473210 A2 | 3/1992 |
| WO | WO-2013/057236 A1 | 4/2013 |

OTHER PUBLICATIONS

Lee et al. The complete unique long sequence and the overall genomic organization of the GA strain of Marek's disease virus. P.N.A.S., May 23, 2000, 97: 6091-6096.*
Islam et al. Quantitative profiling of the shedding rate of the three Marek's disease virus (MDV) serotypes reveals that challenge with virulent MDV markedly increases shedding of vaccinal viruses. Journal of General Virology (2007), 88, 2121-2128.*
Parcells et al "Characterization of Marek's Disease Virus Insertion and Deletion Mutants that Lack US1 (ICP22 Homolog), US10, and/or US2 and Neighboring Short-Component Open Reading Frames" Journal of Virology vol. 68, pp. 8239-8253, 1994.
Sakaguchi et al "Protection of Chickens With or Without Maternal Antibodies Against Both Marek's and Newcastle Diseases by One-Time Vaccination With Recombinant Vaccine of Marek's Disease Virus Type 1" Vaccine vol. 16, pp. 472-479, 1998.
Spatz et al "Comparative Full-Length Sequence Analysis of Oncogenic and Vaccine (Rispens) Strains of Marek's Disease Virus" Journal of General Virology vol. 88, pp. 1080-1096, 2007.
Su et al "Complete Genome Sequence of a Recombinant Marek's Disease Virus Field Strain with One Reticuloendotheliosis Virus Long Terminal Repeat Insert" Journal of Virology vol. 86, pp. 13818-13819, 2012.
Zhang et al "Construction of Recombinant Marek's Disease Virus (MDV) Lacking the meq Oncogene and Co-Expressing AIV-H9N2 HA and NA Genes Under Control of Exogenous Promoters" Journal of Biotechnology vol. 181, pp. 45-54, 2014.
Zhang et al "Transcriptional Activity Comparison of Different Sites in Recombinant Marek's Disease Virus for the Expression of the H9N2 Avian Influenza Virus Hemagglutinin Gene" Journal of Virological Methods vol. 207, pp. 138-145, 2014.
Zhou et al "Protection of Chickens, With or Without Maternal Antibodies, Against IBDV Infection by a Recombinant IBDV-VP2 Protein" Vaccine vol. 28, pp. 3990-3996, 2010.

* cited by examiner

*Primary Examiner* — Nianxiang Zou
(74) *Attorney, Agent, or Firm* — Cesari and McKenna, LLP

(57) ABSTRACT

The present invention relates to recombinant MDV1 viruses and the uses thereof. The invention is particularly suited to vaccinate poultry against avian pathogens.

20 Claims, 9 Drawing Sheets

Specification includes a Sequence Listing.

1: parental Rispens
2: rRispens/MDV096/rpsLneo-DsRed2
3: rRispens/MDV071/rpsLneo-DsRed2
4: rRispens/MDV033/rpsLneo-DsRed2
5: rRispens/MDV015/rpsLneo-DsRed2
6: rRispens/MDV010/rpsLneo-DsRed2
M: Precision Plus Protein All Blue Standards (Bio-Rad, Cat# 161-0373)

Figure 3

1: rRispens/MDV010/rpsLneo-DsRed2
2: rRispens/MDV015/rpsLneo-DsRed2
3: rRispens/MDV033/rpsLneo-DsRed2
4: rRispens/MDV071/rpsLneo-DsRed2
5: rRispens/MDV096/rpsLneo-DsRed2
6: parental Rispens 1: rRispens/MDV010/rpsLneo-DsRed2
2: rRispens/MDV015/rpsLneo-DsRed2
3: rRispens/MDV033/rpsLneo-DsRed2
4: rRispens/MDV071/rpsLneo-DsRed2
5: rRispens/MDV096/rpsLneo-DsRed2
6: parental Rispens IDEXX IBD Ab Test: IDEXX Laboratories NICC = non-immunized, challenged positive controls

SEQUENCE LISTING

<160> NUMBER OF SEQ ID NOS: 51

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ggcctggtga tgatggcggg atcgttgtat                                      30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
ccatggtgct gcgctcagaa gaactcgtca                                      30

<210> SEQ ID NO 3
<211> LENGTH: 1319
<212> TYPE: DNA
<213> ORGANISM: Artificial Sequence
<220> FEATURE:

<223> OTHER INFORMATION: rpsLneo

<400> SEQUENCE: 3

```
ggcctggtga tgatggcggg atcgttgtat atttcttgac accttttcgg catcgcccta      60
aaattcggcg tcctcatatt gtgtgaggac gttttattac gtgtttacga agcaaaagct     120
aaaaccagga gctatttaat ggcaacagtt aaccagctgg tacgcaaacc acgtgctcgc     180
aaagttgcga aaagcaacgt gcctgcgctg gaagcatgcc cgcaaaaacg tggcgtatgt     240
actcgtgtat atactaccac tcctaaaaaa ccgaactccg cgctgcgtaa agtatgccgt     300
gttcgtctga ctaacggttt cgaagtgact tcctacatcg gtggtgaagg tcacaacctg     360
caggagcact ccgtgatcct gatccgtggc ggtcgtgtta aagacctccc gggtgttcgt     420
taccacaccg tacgtggtgc gcttgactgc tccggcgtta aagaccgtaa gcaggctcgt     480
tccaagtatg gcgtgaagcg tcctaaggct taaggaggac aatcatgatt gaacaagatg     540
gattgcacgc aggttctccg gccgcttggg tggagaggct attcggctat gactgggcac     600
aacagacaat cggctgctct gatgccgccg tgttccggct gtcagcgcag ggcgcccgg      660
ttcttttgt caagaccgac ctgtccggtg ccctgaatga actgcaggac gaggcagcgc     720
ggctatcgtg gctggccacg acgggcgttc cttgcgcagc tgtgctcgac gttgtcactg     780
aagcgggaag ggactggctg ctattgggcg aagtgccggg gcaggatctc ctgtcatctc     840
accttgctcc tgccgagaaa gtatccatca tggctgatgc aatgcggcgg ctgcatacgc     900
ttgatccggc tacctgccca ttcgaccacc aagcgaaaca tcgcatcgag cgagcacgta     960
ctcggatgga agccggtctt gtcgatcagg atgatctgga cgaagagcat caggggctcg    1020
cgccagccga actgttcgcc aggctcaagg cgcgcatgcc cgacggcgag gatctcgtcg    1080
tgacccatgg cgatgcctgc ttgccgaata tcatggtgga aaatggccgc ttttctggat    1140
tcatcgactg tggccggctg ggtgtggcgg accgctatca ggacatagcg ttggctaccc    1200
gtgatattgc tgaagagctt ggcggcgaat gggctgaccg cttcctcgtg ctttacggta    1260
tcgccgctcc cgattcgcag cgcatcgcct tctatcgcct tcttgacgag ttcttctga     1319
```

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4

```
acgagttctt ctgagcgcag caccatggcc                                       30
```

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5

```
tcggaggagg ccatccttaa gagctgtaat                                       30
```

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
tacagctctt aaggatggcc tcctccgaga                                            30

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gcagtgaaaa aaatgcttta tttgtgaaat                                            30

<210> SEQ ID NO 8
<211> LENGTH: 70
<212> TYPE: DNA
<213> ORGANISM: Artificial Sequence
<220> FEATURE:
<223> OTHER INFORMATION: Primer

<400> SEQUENCE: 8
catcttcgta ttcgtcactt gcgaaatggc ctggtaatta taacattggg ggcctggtga           60
tgatggcggg                                                                 70

<210> SEQ ID NO 9
<211> LENGTH: 70
<212> TYPE: DNA
<213> ORGANISM: Artificial Sequence
<220> FEATURE:
<223> OTHER INFORMATION: Primer

<400> SEQUENCE: 9
cacaatctct cactcctcaa attgcatttt cagtgctgtt aaatacattc gcagtgaaaa           60
aaatgcttta                                                                 70

<210> SEQ ID NO 10
<211> LENGTH: 70
<212> TYPE: DNA
<213> ORGANISM: Artificial Sequence
<220> FEATURE:
<223> OTHER INFORMATION: Primer

<400> SEQUENCE: 10
atgaataaag tgagacttat aatacttatt gcatagatgt gttttattac ggcctggtga           60
tgatggcggg                                                                 70

<210> SEQ ID NO 11
<211> LENGTH: 70
<212> TYPE: DNA
<213> ORGANISM: Artificial Sequence
<220> FEATURE:
<223> OTHER INFORMATION: Primer

<400> SEQUENCE: 11
tattataaca tacttgtagg taataaacaa actaccoctg taaaaggcaa gcagtgaaaa           60
aaatgcttta                                                                 70

<210> SEQ ID NO 12
<211> LENGTH: 70
<212> TYPE: DNA
<213> ORGANISM: Artificial Sequence
<220> FEATURE:

<223> OTHER INFORMATION: Primer

<400> SEQUENCE: 12
tacctgaaat gtgatcggac ttgggaaaaa tcttcacgcg aaataaattc ggcctggtga    60
tgatggcggg                                                          70

<210> SEQ ID NO 13
<211> LENGTH: 70
<212> TYPE: DNA
<213> ORGANISM: Artificial Sequence
<220> FEATURE:
<223> OTHER INFORMATION: Primer

<400> SEQUENCE: 13
tttaatgcaa aaataaataa agaacctttg ggaataacaa gctatgtata gcagtgaaaa    60
aaatgcttta                                                          70

<210> SEQ ID NO 14
<211> LENGTH: 70
<212> TYPE: DNA
<213> ORGANISM: Artificial Sequence
<220> FEATURE:
<223> OTHER INFORMATION: Primer

<400> SEQUENCE: 14
aaaagttatt agtcatgcaa gcatctgtca aatagcaatc acataatgga ggcctggtga    60
tgatggcggg                                                          70

<210> SEQ ID NO 15
<211> LENGTH: 70
<212> TYPE: DNA
<213> ORGANISM: Artificial Sequence
<220> FEATURE:
<223> OTHER INFORMATION: Primer

<400> SEQUENCE: 15
tttcaatgag gagaaggttc ccctcattat gcagctttga ggcctttgat gcagtgaaaa    60
aaatgcttta                                                          70

<210> SEQ ID NO 16
<211> LENGTH: 70
<212> TYPE: DNA
<213> ORGANISM: Artificial Sequence
<220> FEATURE:
<223> OTHER INFORMATION: Primer

<400> SEQUENCE: 16
gatccgaaaa tatatcatgc aaataagcat gttctagcac cactgcaaca ggcctggtga    60
tgatggcggg                                                          70

<210> SEQ ID NO 17
<211> LENGTH: 70
<212> TYPE: DNA
<213> ORGANISM: Artificial Sequence
<220> FEATURE:
<223> OTHER INFORMATION: Primer

<400> SEQUENCE: 17
tgctcggagg caatggttca actattcttt ccggaaatcg ataaaccaca gcagtgaaaa    60
aaatgcttta                                                          70

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
gtgcgagatt attcctttta aggaatactc                    30

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
ggacaaattt cctcatataa gtggagaag                     29

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
cgagaactga ttgcaggagg gaattcatcc                    30

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
catgtagaca tagacacaca gaatatatcc                    30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
catcatagtt gtatgttcga cgaattaagc                    30

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
tcagaagaac tcgtcaagaa ggc                           23

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
aaatcagatc ggttgtctac ttcgagtatg                                30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
agactatatg cttttcttga atacgactag                                30

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
taaagacatt gatcccatag acgtcgcg                                  28

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
agacatgtaa aatggttgta ctgaaattcg                                30

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
actgatatgt acatatttaa acttaatggg                                30

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
gcgcatgcgc acgcatatag atcgaac                                   27

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
cggccaataa ggcccccaat gttataatta                                30

<210> SEQ ID NO 31
<211> LENGTH: 30

```
<212> TYPE: DNA
<213> ORGANISM: Artificial Sequence
<220> FEATURE:
<223> OTHER INFORMATION: Primer

<400> SEQUENCE: 31
gcgaattcat aacagaatgt cacgataaag                                          30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gggccttatt ggccgaatgt atttaacagc                                          30

<210> SEQ ID NO 33
<211> LENGTH: 274
<212> TYPE: DNA
<213> ORGANISM: Artificial Sequence
<220> FEATURE:
<223> OTHER INFORMATION: Core sequence of chicken beta-actin promoter

<400> SEQUENCE: 33
tattttgtgc agcgatgggg gcggggggggg ggggggcgcg cgccaggcgg ggcggggcgg         60
ggcgaggggc ggggcggggc gaggcggaga ggtgcggcgg cagccaatca gagcggcgcg        120
ctccgaaagt ttcctttat ggcgaggcgg cggcggcggc ggccctataa aaagcgaagc         180
gcgcggcggg cgggagtcgc tgcgcgctgc cttcgccccg tgccccgctc cgccgccgcc        240
tcgcgccgcc cgccccggct ctgactgacc gcgt                                   274

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gagcaacttc gagctgatcc                                                     20

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
gcggtaccgc cctagaactc agccgagt                                            28

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
aggccaataa ggccgtaata aaacacatct                                          30

<210> SEQ ID NO 37
```

```
<211> LENGTH: 30
<212> TYPE: DNA
<213> ORGANISM: Artificial Sequence
<220> FEATURE:
<223> OTHER INFORMATION: Primer

<400> SEQUENCE: 37
gcgagctccg tcttaactat tatgtggatg                                   30

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
cggccttatt ggccttgcct tttacagggg                                   30

<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39
gcggtacctt cgcgagttgt gcgatcatc                                    29

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
aggccaataa ggccgaattt atttcgcgtg                                   30

<210> SEQ ID NO 41
<211> LENGTH: 29
<212> TYPE: DNA
<213> ORGANISM: Artificial Sequence
<220> FEATURE:
<223> OTHER INFORMATION: Primer

<400> SEQUENCE: 41
gcgagctctt tgcccatttc tggactagg                                    29

<210> SEQ ID NO 42
<211> LENGTH: 30
<212> TYPE: DNA
<213> ORGANISM: Artificial Sequence
<220> FEATURE:
<223> OTHER INFORMATION: Primer

<400> SEQUENCE: 42
cggccttatt ggcctataca tagcttgtta                                   30

<210> SEQ ID NO 43
<211> LENGTH: 29
<212> TYPE: DNA
<213> ORGANISM: Artificial Sequence
<220> FEATURE:
<223> OTHER INFORMATION: Primer

<400> SEQUENCE: 43
```

```
gcggtacctc catatatgtt tccgtcctg                                29
```

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44

```
tggccaataa ggcctccatt atgtgattgc                               30
```

<210> SEQ ID NO 45
<211> LENGTH: 28
<212> TYPE: DNA
<213> ORGANISM: Artificial Sequence
<220> FEATURE:
<223> OTHER INFORMATION: Primer

<400> SEQUENCE: 45

```
gcgagctcat aactgcagaa accaaacg                                 28
```

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46

```
aggccttatt ggccatcaaa ggcctcaaag                               30
```

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47

```
gcggtacctt ttactcacat cgctatc                                  27
```

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48

```
aggccaataa ggcctgttgc agtggtgcta                               30
```

<210> SEQ ID NO 49
<211> LENGTH: 29
<212> TYPE: DNA
<213> ORGANISM: Artificial Sequence
<220> FEATURE:
<223> OTHER INFORMATION: Primer

<400> SEQUENCE: 49

```
gcgagctcgc tgcatattgc atcactata                                29
```

<210> SEQ ID NO 50
<211> LENGTH: 30
<212> TYPE: DNA

```
<213> ORGANISM: Artificial Sequence
<220> FEATURE:
<223> OTHER INFORMATION: Primer

<400> SEQUENCE: 50
aggccttatt ggcctgtggt ttatcgattt                                    30

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
gccagggaat ccagggaaaa agac                                          24
```

RECOMBINANT MDV1 AND THE USES THEREOF

CROSS REFERENCE TO RELATED APPLICATIONS

This application is the National Stage of International Application No. PCT/EP2016/051871, filed on Jan. 29, 2016, which claims the benefit of European Application No. 15305102.4, filed on Jan. 29, 2015. The contents of both applications are hereby incorporated by reference in their entirety.

FIELD OF THE INVENTION

The present invention relates to recombinant viruses and the uses thereof. More particularly, the invention relates to novel recombinant Marek's disease viruses of serotype 1, and their use to express or deliver polypeptides of interest to animals, particularly poultry. The invention is particularly suited to vaccinate poultry against avian pathogens.

BACKGROUND OF THE INVENTION

Poultry meat and eggs are important food sources, whose consumption increases continually due to the growth of the human population and their great quality-price ratio. The recent epidemic of avian influenza focused the public opinion on poultry health as well as food safety and security. Poultry vaccine technology became a worldwide concern.

Recombinant viruses expressing pathogen proteins are commonly used as poultry vaccines against targeted pathogens. Vaccines including such viruses induce expression of foreign pathogen proteins or fragments thereof within infected cells, which can subsequently induce a specific and protective humoral immunity as well as cell-mediated immunity.

It is known that different viruses can survive in the body of an infected animal in the state of latent or persistent infection. Consequently, such viruses, in which a foreign gene derived from a pathogen has been integrated, have been developed to be used as viral-vectored vaccines increasing the duration of immunity to an immunized animal. These viral vectors (or recombinant viruses) are based typically on avipox viruses, such as fowlpox (EP-A-0,517,292), herpes viruses, particularly HVT (e.g., WO-A-87/04463, U.S. Pat. Nos. 5,980,906, 5,853,733), Newcastle disease virus (NDV) or avian adenoviruses. These recombinant avian viruses display variable levels of protection. In particular, because Poxviruses, NDV, and adenoviruses do not persist in chickens, long duration of immunity is not expected. A recombinant HVT expressing IBDV VP2 has shown advantages over classical IBD vaccines (Vectormune® IBD). Other HVT vectors of interest express NDV (Vectormune® ND) or ILTV (Vectormune® LT) antigens.

One of the practical problems of HVT-based recombinant viruses is their interference when several viruses are used in combination to confer immunogenicity against distinct pathogens. Indeed, when two distinct rHVT expressing different antigens are mixed, a lower protection is caused at least against one of the disease (see e.g., Slacum G et al., 2009, The compatibility of HVT recombinants with other Marek's disease vaccines, 58th Western Poultry Disease Conference, Sacramento, Calif., USA, March 23-25, p 84).

Multivalent HVT vectors have been developed which can express two distinct antigenic peptides (see PCT/EP2013/056839) and potentially overcome the limitations of the prior art. Also, new viral serotypes are being explored, with the aim to find alternative compatible viral vectors. In this regard, MDV1 has been experimentally used but the recombinants generated so far did not provide satisfactory results.

Accordingly, there is still a need for new alternative approaches to improve vaccination in animals, particularly in poultry, allowing stable protein expression and, preferably concomitant protection against several diseases.

SUMMARY OF THE INVENTION

The present invention discloses novel recombinant viruses suitable to induce strong immune protection in animals and which may, in addition, be used in combination with other viral vaccines to procure extended immunity. The present invention more specifically relates to novel recombinant Marek's disease viruses of serotype 1 ("rMDV1"). The invention discloses novel genetic regions within the MDV1 genome which allow effective cloning and stable expression of foreign genes.

An object of the invention therefore resides in a recombinant Marek's Disease Virus serotype 1 (rMDV1) comprising a foreign gene in its genome, wherein said foreign gene is positioned in an untranslated genetic region of the genome. More preferably, the untranslated genetic region is located between MDV010 and MDV016, between MDV033 and MDV034, between MDV071 and MDV072, or between MDV096 and MDV097.6 in the viral genome.

As disclosed in the experimental section, such constructs allow highly improved expression and induction of strong protective immunity. Furthermore, the viruses of the invention may be used in combination with other viruses such as HVT without cross-interference, thereby causing extended immunity.

A further object of the invention relates to a nucleic acid molecule comprising the genome of a rMDV1 as defined above.

The invention also relates to a plasmid comprising a nucleic acid molecule as defined above.

Another object of the invention is a host cell, or a culture of such cells, comprising a nucleic acid molecule or a plasmid or a virus as defined above.

A further object of the invention is a method for producing or replicating a rMDV1, comprising infecting a competent cell with a nucleic acid molecule or with a rMDV1 as defined above and collecting the rMDV1.

A further object of the invention is a method for producing a rMDV1 expressing a foreign gene, the method comprising inserting the foreign gene in an untranslated genetic region of the genome, preferably located between MDV010 and MDV016, between MDV033 and MDV034, between MDV071 and MDV072, or between MDV096 and MDV097.6.

Another object of the invention resides in a composition comprising a rMDV1 or a nucleic acid as defined above and a pharmaceutically or veterinary acceptable excipient or carrier.

A further object of the invention relates to a vaccine composition comprising a rMDV1 or a nucleic acid as defined above, a pharmaceutically or veterinary acceptable excipient or carrier and, optionally, a suitable adjuvant. Such a vaccine can be used e.g., for immunizing avians, such as poultry.

Another object of the invention resides in a rMDV1 or composition or vaccine as defined above for use to vaccinate an avian, preferably a chicken.

Another object of the invention resides in a rMDV1 or composition or vaccine as defined above for use to induce or stimulate an immune response in an avian, preferably a chicken.

A further object of the invention is a recombinant MDV1 as defined above, for use in combination with a further recombinant herpes virus of a distinct serotype and expressing a distinct antigen, to vaccinate an avian, preferably a chicken, by simultaneous, separate sequential or alternated administration.

In another aspect, the invention provides a method of vaccinating an animal comprising administering to said animal a composition, vaccine or virus as defined above.

In a further aspect, the invention provides a method for inducing an immunogenic or protective response in an animal against one or more avian pathogens comprising administering to said animal a composition, vaccine or virus as defined above.

The invention further provides a vaccination kit for immunizing an avian which comprises an effective amount of a vaccine of the invention and a means for administering said vaccine to said avian.

The invention may be used for expressing a polypeptide in any animal, preferably for the vaccination of an avian, and it is suitable for expressing one or several polypeptides or peptides, particularly immunogenic peptides of avian pathogens. The recombinant MDV1 of the invention is preferably a Rispens strain.

LEGEND TO THE FIGURES

DETAILED DESCRIPTION OF THE INVENTION

Figure 1:
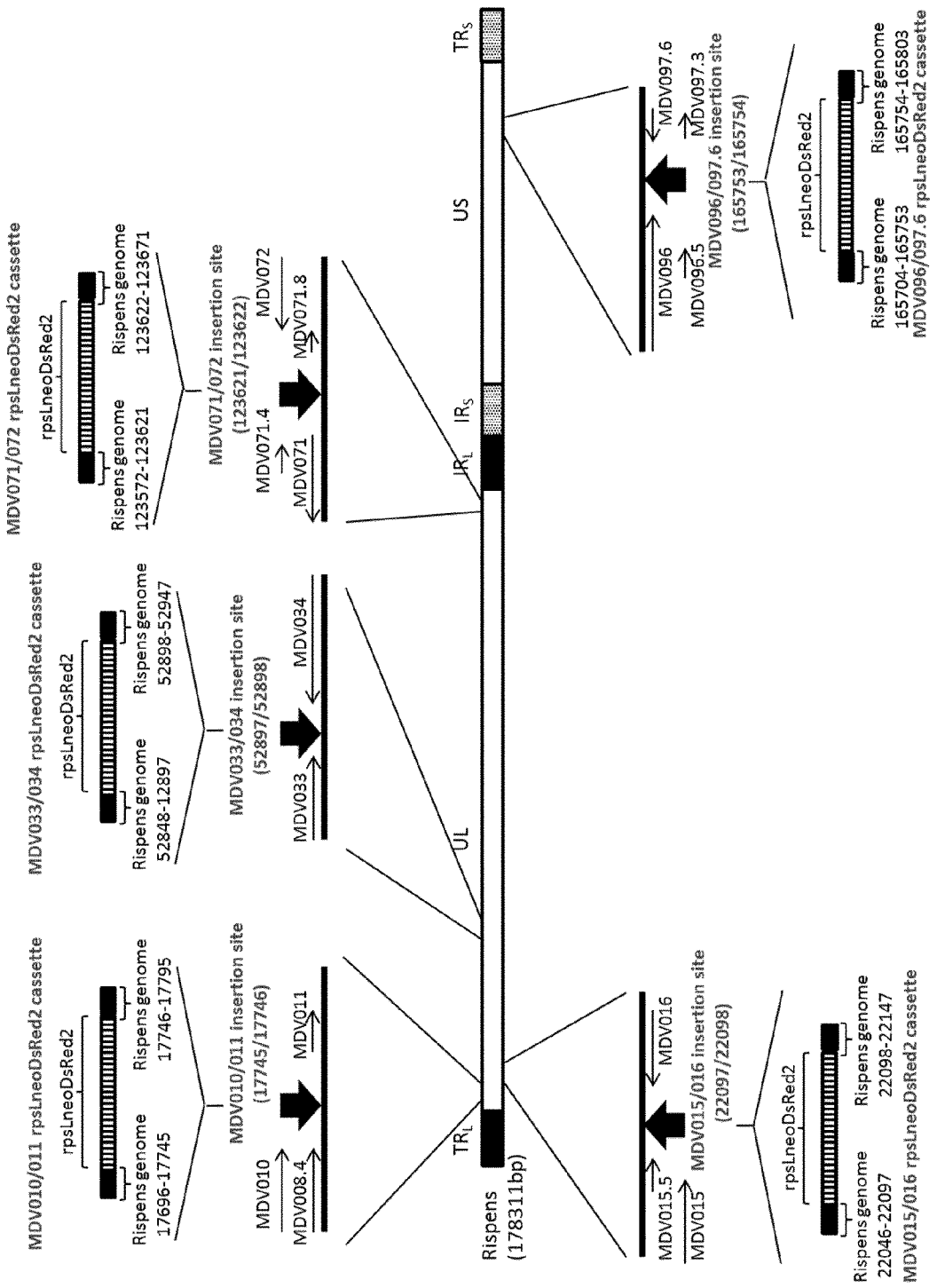
FIG. 1 illustrates a schematic diagram of the Rispens genome and the location of the cloned region of recombinant Rispens/rpsLneo-DsRed2 including the insertion site.

The present invention generally relates to rMDV1 which comprise foreign gene sequence(s) located in particular insertion sites within the genome. The present invention also relates to compositions comprising such rMDV1, as well as to the use thereof for vaccination of animals, particularly poultry.

The present disclosure will be best understood by reference to the following definitions:

Definitions

The term "virus" designates in particular a viral particle comprising a nucleic acid molecule (e.g., a genome) encapsulated in a capsid or capsule. The term "virus" also designates a viral vector or an isolated viral genome.

The term "recombinant" designates a molecule which has been created, designed or modified using genetic technologies. In relation to a virus, the term "recombinant" more specifically designates a virus whose genome (or whose ancestor's genome) has been modified by insertion of at least one foreign nucleic acid, i.e., a nucleic acid (e.g., DNA) which is not found naturally in the genome of the virus, or which is found naturally in said genome but in a different form or at a different position.

In the present description, the term "nucleic acid" or "nucleic acids" designates any nucleic acid molecule such as deoxyribonucleotide (DNA) or ribonucleotide (RNA), which may be e.g., single- or double-stranded. Nucleic acids may comprise an ORF or not. Nucleic acid molecules may be produced by techniques known per se in the art such as by artificial synthesis, recombinant technology, enzymatic technology, replication in host cells, or combinations thereof.

A "gene" designates a nucleic acid molecule or sequence which comprises an open reading frame encoding a product, such as a polypeptide (e.g., a peptide, protein, etc.) or an RNA.

The term "untranslated genetic region" as used herein refers to a region in a nucleic acid sequence or molecule that is not part of a coding sequence. The term "untranslated genetic region" as used herein thus encompasses non-coding regions in a viral genome, but does not encompass ORFs.

The term "avian" is intended to encompass all kinds of avians such as birds of the class of Aves, i.e., vertebrate animals which are feathered, winged, bipedal, endothermic and egg-laying. In the context of the invention, avians or avian species refer more particularly to birds with economical and/or agronomical interests, such as poultry, (such as chickens and turkeys), waterfowl poultry (such as ducks and geese) and ornamental birds (such as swans and psittacines).

The term "vaccine" as used herein designates an agent which may be used to cause, stimulate or amplify an immune response in an organism.

An "immune response" designates the development in a host of a cellular and/or antibody-mediated immune response to a composition or vaccine of interest. Usually, an "immune response" includes the production of antibodies, B cells, helper T cells, and/or cytotoxic T cells, directed specifically to an antigen or antigens included in the composition or vaccine of interest. Preferably, the immune response is protective such that resistance to new infection will be enhanced and/or the clinical severity of the disease reduced.

Marek's Disease Viruses Serotype 1

Marek's Disease Viruses serotype 1 are avian herpes viruses. They belong to a larger group of Marek Disease viruses, which notable include serotype 2 and serotype 3, HVTs. Although HVTs have been extensively studied, MDV1 are less characterized. In particular, much less use has been made of this virus and there are few reports of suitable recombinants thereof. In this regard, prior attempts to use this virus essentially tried to clone a foreign sequence within a gene (e.g., UL43) or within a regulatory domain (e.g., long IR) of the genome. Such recombinants, however, did not turn out to generate stable or potent expression. As a result, MDV1 has attracted less attention than other viruses such as, for instance, HVT.

The present inventors conducted further research with MDV1 and were able to generate stable recombinants. More particularly, the inventors found that stable recombinants can be generated when a foreign sequence is cloned into an untranslated genetic region of the genome. With such recombinants, strong foreign gene expression can be achieved in vitro, and a very potent protective immune response (up to 100% protection) can be obtained in vivo. Such new recombinants thus represent highly valuable vectors for gene transfer and expression in vivo, particularly in poultry, most preferably for vaccination purposes.

The present invention thus relates to recombinant MDV1 comprising a foreign nucleic acid cloned into an untranslated genetic region.

rMDV1 of the invention may be prepared from any MDV1, preferably from serotypes or strains that are non-pathogenic to targeted animal (e.g., avian) species. A number of strains of MDV1 have been reported, which are available from public collections, such as the CVI988/Rispens strain, C2 strain and R2/23 strain.

In a preferred embodiment, the rMDV1 is a Rispens strain MDV1, more preferably CVI988 strain (see complete genome; GenBank: DQ530348.1; Spatz et al, Journal of General Virology (2007), 88, 1080-1096), or any MDV1 having at least 90% sequence identity to CVI988 strain, more preferably at least 95%, at least 96%, at least 97%, at least 98%, or at least 99%.

The foreign nucleic acid may be cloned into any untranslated genetic region of the MDV1 genome. Most preferably, however, the nucleic acid is cloned in an untranslated genetic region located between MDV010 and MDV016, between MDV033 and MDV034, between MDV071 and MDV072, or between MDV096 and MDV097.6 of the genome. The invention indeed shows that these particular untranslated regions represent potent sites for nucleic acid insertion without preventing effective viral replication and infection, and allowing effective expression in vivo of products of interest.

In a more particular embodiment, the foreign nucleic acid is located in an untranslated genetic region located between MDV010 and MDV011, between MDV015.5 and MDV016, between MDV033 and MDV034, between MDV071 and MDV072, or between MDV096 and MDV097.6 of the genome.

Further preferably, the foreign nucleic acid is located in an untranslated genetic region located between MDV010 and MDV011, between MDV015.5 and MDV016, or between MDV071 and MDV072.

The untranslated genetic region located between MDV010 and MDV011 typically corresponds to nt17324 to nt17878 of the MDV1 genome. Cloning may be performed at any position within such domain, more preferably between nt17500 and nt17850, furthermore preferably between nt17700 and nt17800. In a specific embodiment, cloning is performed between nt17745 and nt17746 (e.g., RR043 and rRispens/MDV010/rpsLneo-DsRed2).

The untranslated genetic region located between MDV015.5 and MDV016 typically corresponds to nt21940 to nt22256 of the MDV1 genome. Cloning may be performed at any position within such domain, more preferably between nt22000 and nt22200, furthermore preferably between nt22050 and nt22150. In a specific embodiment, cloning is performed between nt22097 and nt22098 (e.g., RR044 and rRispens/MDV015/rpsLneo-DsRed2).

The untranslated genetic region located between MDV033 and MDV034 typically corresponds to nt52797 to nt52942 of the MDV1 genome. Cloning may be performed at any position within such domain, more preferably between nt52800 and nt52950, furthermore preferably between nt52850 and nt52950. In a specific embodiment, cloning is performed between nt52897 and nt52898 (e.g., RR045 and rRispens/MDV033/rpsLneo-DsRed2).

The untranslated genetic region located between MDV071 and MDV072 typically corresponds to nt123273 to nt123904 of the MDV1 genome. Cloning may be performed at any position within such domain, more preferably between nt123400 and nt123800, furthermore preferably between nt123500 and nt123700. In a specific embodiment, cloning is performed between nt123621 and nt123622 (e.g., RR046 and rRispens/MDV071/rpsLneo-DsRed2).

The untranslated genetic region located between MDV096 and MDV097.6 typically corresponds to nt165464 to nt166202 of the MDV1 genome. Cloning may be performed at any position within such domain, more preferably between nt165500 and nt166000, furthermore preferably between nt165700 and nt165800. In a specific embodiment, cloning is performed between nt165753 and nt165754 (e.g., RR047 and rRispens/MDV096/rpsLneo-DsRed2).

It should be noted that the skilled artisan may identify, from any MDV1 strain, the corresponding positions of the cloning site by mere sequence alignment.

The foreign nucleic acid may be cloned in the MDV1 in replacement of all or a portion (e.g., from 1 to 500 nt) of the untranslated genetic region, or without deletion of said untranslated genetic region.

Furthermore, the rMDV1s of the invention may comprise several foreign genes.

In the rMDV1s of the invention, the foreign gene is generally under control of a transcriptional promoter. Preferably the promoter is cloned with the foreign gene. The promoter may be any natural or synthetic promoter, derived from cellular or viral genes. Examples of suitable promoters include, for instance, the chicken beta-actin (Bac) promoter or a derivative thereof such as Coa5, the Pec promoter, the Murine Cytomegalovirus (Mcmv) immediate-early (ie)1 promoter, the Human Cytomegalovirus promoter (Hcmv), the Simian virus (SV)40 promoter, and the Rous Sarcoma virus (RSV) promoter, or any fragments thereof which retain a promoter activity.

Virus construction and cloning may be accomplished by techniques know per se in the art. Gene cloning and plasmid construction are well known to one person of ordinary skill in the art and may be essentially performed by standard molecular biology techniques (*Molecular Cloning*: A Laboratory Manual. 4th Edition, Cold Spring Harbor Laboratory, Cold Spring Harbor, N.Y., USA, 2012). Typically, the recombinant viruses may be prepared by homologous recombination between the viral genome and a construct (e.g., a homology plasmid) comprising the nucleic acid to be inserted, flanked by nucleotides from the insertion site to allow recombination. Cloning can be made with or without deletion of endogenous sequences. In a particular embodiment, the recombinant sequence is cloned in replacement of at least part of a sequence of the genome, such as at least 50 nucleotides or more. Such deletion increases the cloning capacity of the virus.

For construction, a sequence containing the targeted insertion region is typically first cloned into a suitable vector to produce a homology vector. Examples of vectors include plasmids, such as pBR322, pBR325, pBR327, pBR328, pUC18, pUC19, pUC7, pUC8, or pUC9; phages such as lambda phage and M13 phage; or cosmids such as pHC79. The target region sequence is integrated into the vector by conventional cloning methods. The target region sequence used is preferably of sufficient length so as to allow subsequent in vivo homologous recombination with the viral genome. Preferably, the cloned target region sequence shall have at least approximately 100 nucleotides in length, typically above 300, such as between 500 and 2000 nucleotides. The foreign nucleic acid (which typically contains a gene and a promoter) is then inserted into the target region cloned in the vector. Insertion shall be made preferably in a manner that leaves a portion of sequence of the target region on each side of the cloned insert of a length sufficient to allow homologous recombination (e.g. of at least 50 nucleotides, preferably of at least 100 nucleotides). The foreign nucleic acid can be introduced into the cloned target region by classical techniques such as restriction enzyme and ligation procedures. If appropriate, mutation(s) may be introduced at a specific site of the target region to create a new cleavage site for a restriction enzyme. Conventional mutagenesis techniques well known by a person skilled in the art may be used for that purpose, such as e.g., in vitro mutagenesis or PCR. Homology vectors in which the foreign nucleic acid has been inserted into the target region may then be introduced into an MDV1-infected cell or MDV1 genome-transfected cells using known techniques such as electroporation, calcium phosphate, lipofectin-based method, or the like. The recombinant viruses are thereby produced by recombination in said cells between the virus and the vector. The resulting recombinant virus may be selected genotypically or phenotypically using known techniques, e.g., by hybridization, sequencing, PCR or a functional assay to detect any product encoded by the foreign nucleic acid. The selected recombinant virus can be cultured on a large scale in cell culture after which, recombinant viruses can be collected.

Foreign Gene

The rMDV1 of the invention may contain any foreign nucleic acid, preferably any foreign gene. The foreign gene may encode any product of interest such as RNAs or biologically active and/or immunogenic (e.g., antigenic) proteins, polypeptides or peptides. In a preferred embodiment, the foreign gene encodes an antigen, even more preferably a peptide or polypeptide derived from an antigen of a pathogenic organism capable of causing an infection in an animal, particularly an avian. Examples of pathogens that cause infection in avian include viruses, bacteria, fungi, protozoa, etc. The immunogenic (poly)peptide may preferably be (derived from) a surface protein, a secreted protein, or a structural protein of said pathogen, or fragments thereof. The polypeptide can be derived from any source, e.g., viral, prokaryotic, eukaryotic or synthetic.

In a preferred embodiment, the foreign gene encodes an antigenic peptide of a bird pathogenic agent.

Specific examples of pathogenic agents include, without limitation, avian influenza virus, avian paramyxovirus type 1, also called Newcastle disease virus (NDV), avian metapneumovirus, Marek's disease virus, Gumboro disease virus, also called infectious bursal disease virus (IBDV), Infectious laryngotracheitis virus (ILVT), Infectious bronchitis virus (IBV), *Escherichia coli*, *Salmonella* species, *Pasteurella multocida*, *Riemerella anatipestifer*, *Ornnithobacterium rhinotracheale*, *Mycoplasma gallisepticum*, *Mycoplasma synoviae*, Mycoplasmas microorganisms infecting avian species or coccidian.

Preferentially, the foreign gene encodes an antigen selected from the F protein of NDV, the HN protein of NDV, the VP2 protein of IBDV, the gB protein of ILTV, the 40K protein of *Mycoplasma galisepticum*, or the surface protein hemagglutinin (HA) of the avian influenza virus, or immunogenic fragments thereof. Within the context of the invention, the term "fragment" of a protein designates preferably a fragment comprising at least 5 consecutive amino acid residues of said protein, even more preferably from 5-100. In a preferred embodiment, such a fragment comprises at least one epitope and/or is immunogenic in vivo, i.e., can cause production of antibodies that bind the full length protein.

Specific examples of immunogenic peptides include, for instance, a peptide comprising amino acid residues 1-453 of entire VP2.

Preferred rMDV1s

A preferred rMDV1 of the invention comprises at least one foreign gene encoding an avian antigen cloned in an untranslated genetic region located between MDV010 and MDV011. Preferably, the avian antigen is a VP2, HN or F protein or an immunogenic fragment thereof.

Another preferred rMDV1 of the invention comprises at least one foreign gene encoding an avian antigen cloned in an untranslated genetic region located between MDV015.5 and MDV016. Preferably, the avian antigen is a VP2, HN or F protein or an immunogenic fragment thereof.

A preferred rMDV1 of the invention comprises at least one foreign gene encoding an avian antigen cloned in an untranslated genetic region located between MDV033 and MDV034. Preferably, the avian antigen is a VP2, HN or F protein or an immunogenic fragment thereof.

A preferred rMDV1 of the invention comprises at least one foreign gene encoding an avian antigen cloned in an untranslated genetic region located between MDV071 and MDV072. Preferably, the avian antigen is a VP2, HN or F protein or an immunogenic fragment thereof.

A preferred rMDV1 of the invention comprises at least one foreign gene encoding an avian antigen cloned in an untranslated genetic region located between MDV096 and MDV097.6. Preferably, the avian antigen is a VP2, HN or F protein or an immunogenic fragment thereof.

Cell Cultures

The recombinant viruses of the present invention may be propagated in any competent cell cultures. After required growth of the viruses is achieved, the cells may be detached from the wells using a scraper or with trypsin and the infected cells may be separated from the supernatant by centrifugation.

Examples of competent cells include CEF, embryonated egg, chicken kidney cell, and the like. The cells or viruses may be cultured in a culture medium such as Eagle's MEM, Leibowitz-L-15/McCoy 5A (1:1 mixture) culture medium at about 37° C. for 3 to 6 days. The infected cells are typically suspended in a culture medium containing 10% dimethyl sulfoxide (DMSO) and stored frozen under liquid nitrogen.

Compositions and Vaccines

The invention also relates to compositions, such as vaccines, which comprise one or more recombinant MDV1 of the invention.

Compositions of the invention may comprise the rMDV1 in a pharmaceutically or veterinary acceptable vehicle or excipient. The composition may, in addition or alternatively, comprise a suitable adjuvant.

The rMDV1s of the invention may be used in live form (e.g., to prepare live vaccines) or, alternatively, in inactivated, attenuated, or killed form. The production of such forms is known in the art.

The vaccine according to the present invention may further comprise a suitable solvent, such as for example an aqueous buffer or a phosphate buffer. Preferably, the vaccine also comprises additives. Additives of the present invention may be obtained from any of a number of sources including various proteins and peptides derived from animals (e.g., hormones, cytokines, co-stimulatory factors), and novel nucleic acids derived from viruses and other sources (e.g., double stranded RNA, CpG), and the like which are administered with the vaccine in an amount sufficient to enhance the immune response. In addition, any number of combinations of the aforementioned substances may provide an immunopotentiation effect, and therefore, can form an immunopotentiator of the present invention.

The vaccines of the present invention may further be formulated with one or more further additives to maintain isotonicity, physiological pH and stability, for example, a buffer such as physiological saline (0.85%), phosphate-buffered saline (PBS), citrate buffers, Tris(hydroxymethyl aminomethane (TRIS), Tris-buffered saline and the like, or an antibiotic, for example, neomycin or streptomycin, etc.

The route of administration can be any route including oral, ocular (e.g., by eyedrop), oculo-nasal administration using aerosol, intranasal, Cloacal in feed, in water, or by spray, in ovo, topically, or by injection (e.g., intravenous, subcutaneous, intramuscular, intraorbital, intraocular, intradermal, and/or intraperitoneal) vaccination. The skilled person will easily adapt the formulation of the vaccine composition for each type of route of administration.

Each vaccine dose may contain a suitable dose sufficient to elicit a protective immune response in avian species. Optimization of such dose is well known in the art. The amount of antigen per dose may be determined by known methods using antigen/anti-body reactions, for example by the ELISA method.

The vaccines of the invention can be administered as single doses or in repeated doses, depending on the vaccination protocol.

The vaccines of the present invention are further advantageous in that they confer to bird species up to 80% protection against the targeted avian pathogens.

The present invention further relates to the use of the vaccine as described above for immunizing avian species, such as poultry, and to method of immunizing avian species by administering an immunologically effective amount of the vaccine according to the invention. The vaccine may be advantageously administered intradermally, subcutaneously, intramuscularly, orally, in ovo, by mucosal administration or via oculo-nasal administration.

The present invention further relates to vaccination kits for immunizing avian species which comprises an effective amount of the multivalent vaccine as described above and a means for administering said components to said species. For example, such kit comprises an injection device filled with the vaccine according to the invention and instructions for intradermic, subcutaneous, intramuscular, or in ovo injection. Alternatively, the kit comprises a spray/aerosol or eye drop device filled with the vaccine according to the invention and instructions for oculo-nasal administration, oral or mucosal administration.

Further aspects and advantages of the invention will be disclosed in the following experimental section, which is illustrative of the claimed invention.

EXAMPLES

Example 1: Construction Of rpsLneo-DsRed2 Expression Cassette

A 2.8-kb DNA fragment of rpsLneo-DsRed2 cassette was constructed by PCR reactions (FIG. 1). Briefly, three PCR reactions were conducted. First PCR reaction was conducted using primer pair of SEQ ID NO: 1 (5'-GGCCTGGTGAT-GATGGCGGGATCGTTGTAT-3') and SEQ ID NO: 2 (5'-CCATGGTGCTGCGCTCAGAAGAACTCGTCA-3') with the template of synthesized fragment of rpsLneo (SEQ ID NO: 3). Second PCR reaction was conducted using primer pair of SEQ ID NO: 4 (5'-ACGAGTTCTTCTGAGCGCA-GCACCATGGCC-3') and SEQ ID NO: 5 (5'-TCGGAG-GAGGCCATCCTTAAGAGCTGTAAT-3') with the template plasmid of pSI Mammalian Expression Vectors (Promega, Cat# E1721). Third PCR reaction was conducted using primer pair of SEQ ID NO: 6 (5'-TACAGCTCT-TAAGGATGGCCTCCTCCGAGA-3') and SEQ ID NO: 7 (5'-GCAGTGAAAAAAATGCTTTATTTGTGAAAT-3') with the template plasmid of pIRES2-DsRed2 (Clontech, Cat#632420). Another PCR reaction was conducted using a mixture of PCR products from the first and second PCR reactions as a template and SEQ ID NO: 1 and SEQ ID NO: 5 as primers. This PCR product and the PCR product from third PCR reaction were mixed and used for final PCR reaction with primer pair of SEQ NO: 1 and SEQ NO: 7, resulting in rpsLneo-DsRed2 cassette.

Example 2: Construction of Insertion Cassettes

Five DNA fragments of rpsLneo-DsRed2 cassettes to which were added Rispens MDV010/011, MDV015.5/016, MDV033/034, MDV071/072, or MDV096/097.6 intergenic regions homologous sequences (50 bp each) to both 5' and 3' side of them were constructed by PCR reactions (FIG. 1). Five PCR reactions were conducted using rpsLneo-DsRed2 cassette as a template. Primer pairs used are SEQ ID NO: 8 (5'-CATCTTCGTATTCGTCACTTGCGAAATGGCCTG-GTAATTATAACATTGGGGG CCTGGTGATGATG-GCGGG-3') and SEQ ID NO: 9 (5'-CACAATCTCT-CACTCCTCAAATTGCATTTTCAGTGCTGTTAATA-CATTCGC AGTGAAAAAAATGCTTTA-3') for insertion site MDV010/011, SEQ ID NO: 10 (5'-ATGAATAAAGT-GAGACTTATAATACTTATTGCATAGATGTGTTTTAT-TACGG CCTGGTGATGATGGCGGG-3') and SEQ ID NO: 11 (5'-TATTATAACATACTTGTAGGTAATAAACAAAC-TACCCCTGTAAAAGGCAAG CAGTGAAAAAAAT-GCTTTA-3') for insertion site MDV015/016, SEQ ID NO: 12 (5'-TACCTGAAATGTGATCGGACT-TGGGAAAAATCTTCACGCGAAATAAATTCG GCCTGGTGATGATGGCGGG-3') and SEQ ID NO: 13 (5'-TTTAATGCAAAAATAAATAAAGAAC-CTTTGGGAATAACAAGCTATGTATAG CAGT-GAAAAAAATGCTTTA-3') for insertion site MDV033/034, SEQ ID NO: 14 (5'-AAAAG-TTATTAGTCATGCAAGCATCTGTCAAATAGCAATCA-CATAATGGAG GCCTGGTGATGATGGCGGG-3') and SEQ ID NO: 15 (5'-TTTCAATGAGGAGAAGGTTC-CCCTCATTATGCAGCTTTGAGGCCTTTGATGC AGT-GAAAAAAATGCTTTA-3') for insertion site MDV071/072, or SEQ ID NO: 16 (5'-GATC-CGAAAATATATCATGCAAATAAGCATGTTCTAGCAC-CACTGCAACAG GCCTGGTGATGATGGCGGG-3') and SEQ ID NO: 17 (5'-TGCTCGGAGGCAATGGTTCAACT-ATTCTTTCCGGAAATCGATAAACCACAGC AGT- GAAAAAAATGCTTTA-3') for insertion site MDV096/097.6. Obtained PCR fragments were electrophoresed and purified.

Example 3: Construction of Recombinant Rispens Carrying rpsLneo-DsRed2 Gene

Figure 2:
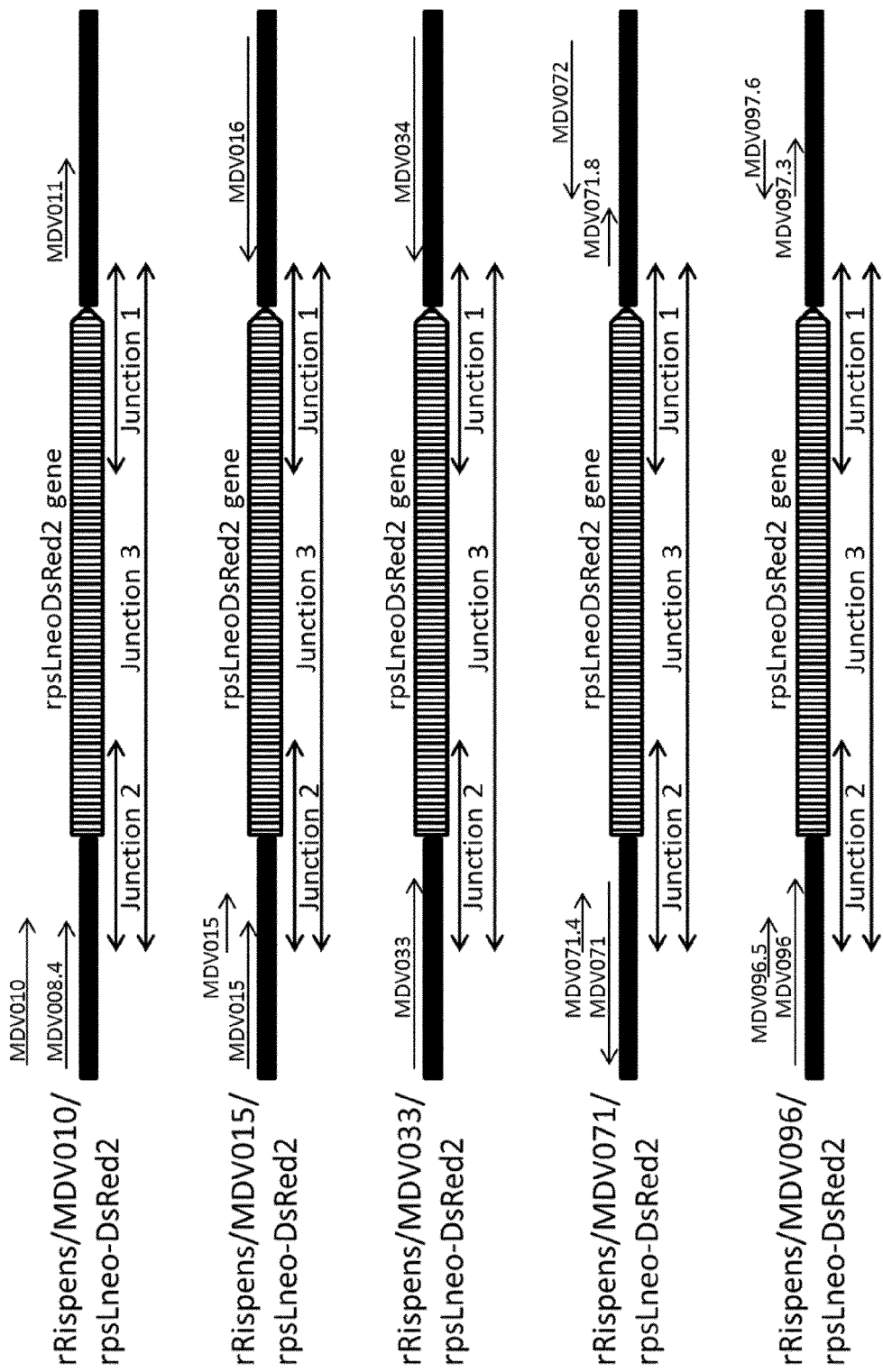
FIG. 2 shows a diagram of recombinant Rispens/rpsLneo-DsRed2 genome, indicating locations of Junction 1, Junction 2, and Junction 3 amplified in PCR reactions to confirm the genome structures of the viruses.

Construction of recombinant Rispens carrying rpsLneo-DsRed2 gene was conducted by homologous recombination in E. coli. DH10B E. coli strain carrying Rispens genome as bacterial artificial chromosomes (BAC) was transfected with 0.1 μg of one of the insertion cassettes. Transfection was conducted by electroporation using Gene Pulser Xcell (Bio-Rad Laboratories) at 1.75 kV, 25 μF, and 200 ohm. After transfection, the E. coli was planted onto Luria-Bertani (LB) agar plates, and incubated overnight at 30° C. E. coli clones carrying an appropriate insert containing the rpsLneo-DsRed2 gene were identified by PCR using each primer pair amplifying a region between rpsLneo-DsRed2 gene and the insertion site region of Rispens genome (FIG. 2). The primers are SEQ ID NO: 6 and SEQ ID NO: 18 (5'-GTGCGAGATTATTCCTTTTAAGGAATACTC-3') for insertion site MDV010/011, SEQ ID NO: 19 (5'-GGACAAATTTCCTCATATAAGTGGAGAAG-3') for insertion site MDV015/016, SEQ ID NO: 20 (5'-CGAGAACTGATTGCAGGAGGGAATTCATCC-3') for insertion site MDV033/034, SEQ ID NO: 21 (5'-CATGTAGACATAGACACACAGAATATATCC-3') for insertion site MDV071/072, or SEQ ID NO: 22 (5'-CATCATAGTTGTATGTTCGACGAATTAAGC-3') for insertion site MDV096/097.6, respectively. Modified Rispens BAC DNA was extracted from E. coli clones carrying an appropriate insert and transfected into CEF cells using Nucleofector II (Lonza, Basel, Switzerland). The transfected cells were added to Leibovitz's L-15 (Life Technologies Corp., Cat. #41300-39), McCoy's 5A Medium (Life Technologies Corp., Cat. #21500-061) (1:1) and 4% calf serum [LM (+) medium], planted in 96-well tissue culture plates, and then incubated at 37° C. in 4-5% $CO_2$ for 5-7 days until Rispens plaques became visible.

Example 4: Verification of Genome Structure

Genome structures of the recombinant Rispens/rpsLneo-DsRed2 were verified by three PCR amplifying junction regions (Junction 1, Junction 2, and Junction 3; FIG. 2) at each end of the inserted genes. The primer pairs used in the PCR reactions for Junction 1 are described in Experiment 3. The primer pairs used in the PCR reactions for Junction 2 are SEQ ID NO: 23 (5'-TCAGAAGAACTCGTCAAGAAGGC-3') and SEQ ID NO: 24 (5'-AAATCAGATCGGTTGTCTACTTCGAGTATG-3') for rRiepens/MDV010/rpsLneo-DsRed2, SEQ ID NO: 25 (5'-AGACTATATGCTTTTCTTGAATACGACTAG-3') for rRiepens/MDV015/rpsLneo-DsRed2, SEQ ID NO: 26 (5'-TAAAGACATTGATCCCATAGACGTCGCG-3') for rRiepens/MDV033/rpsLneo-DsRed2, SEQ ID NO: 27 (5'-AGACATGTAAAATGGTTGTACTGAAATTCG-3') for rRiepens/MDV071rpsLneo-DsRed2, or SEQ ID NO: 28 (5'-ACTGATATGTACATATTTAAACTTAATGGG-3') for rRispens/MDV096/rpsLneo-DsRed2, respectively. For Junction 3, SEQ ID NO: 18 and SEQ ID NO: 24 (rRispens/MDV010/rpsLneo-DsRed2), SEQ ID NO: 19 and SEQ ID NO: 25 (rRispens/MDV015/rpsLneo-DsRed2), SEQ ID NO: 20 and SEQ ID NO: 26 (rRispens/MDV033/rpsLneo-DsRed2), SEQ ID NO: 21 and SEQ ID NO: 27 (rRispens/MDV071/rpsLneo-DsRed2), or SEQ ID NO: 22 and SEQ ID NO: 28 (rRispens/MDV096/rpsLneo-DsRed2), respectively, are used. Expected sizes of PCR products were observed with all of the recombinant Rispens/rpsLneo-DsRed2, confirming that these recombinant Rispens/rpsLneo-DsRed2 have the expected genome structures.

Example 5: Expression of DsRed2 by Recombinant Rispens/rpsLneo-DsRed2

Expression of the DsRed2 protein by the recombinant Rispens/rpsLneo-DsRed2 was confirmed by excitation for DsRed2 or Western blot assay. Excitation for DsRed2 was conducted using CEF cells infected with the recombinant Rispens. Briefly, CEF cells in 6-well plates were infected with one of the recombinant viruses or the parent Rispens strain at a multiplicity of infection of approximately 0.001. Five days post inoculation, cells were excited at 563 nm. Red fluorescence was only observed in the plaques of recombinant Rispens/rpsLneo-DsRed2. These cells infected with the parent Rispens or one of the recombinant viruses were also used for western blot assay. Briefly, the cells were harvested with trypsin and centrifuged at 913×g for 5 minutes. The pellet was washed with PBS and resuspended with 50 μl of PBS. After adding the same volume of 2×SDS sample buffer (130 mM Tris-Cl (pH 6.8), 6% SDS, 20% Glycerol, 10% 2-Mercaptoethanol and 0.01% Bromo Phenol Blue), cell suspension was boiled for 5 minutes. The samples were separated by SDS-PAGE using 12% polyacrylamide gel and transferred to a PVDF membrane (Immobilon-P, Millipore). The membrane was dried completely and then incubated with the anti-DsRed monoclonal antibody (Living Colors® DsRed Monoclonal Antibody, TaKaRa). After the anti-DsRed monoclonal antibody was washed off, the membrane was incubated with biotinylated anti-mouse IgG antibody (Vector Laboratories, Cat#BA-9200) and then with VECTASTAIN ABC-AP kit (Vector Laboratories, Cat#AK-5000). Protein bound with the anti-DsRed monoclonal antibody was visualized by addition of NBT/BCIP solution (Roche Applied Science, Cat#1681451).

Figure 3:
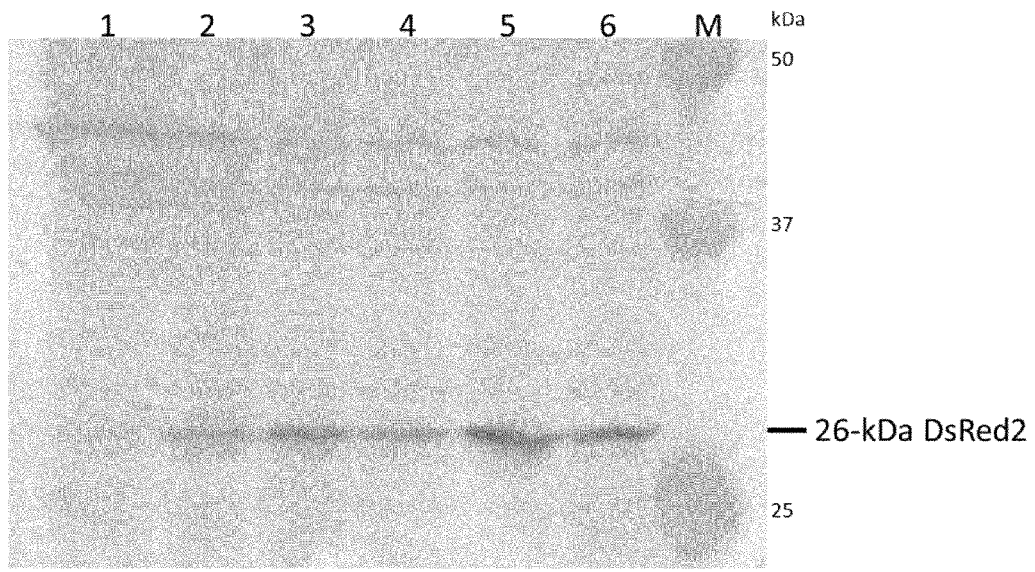
FIG. 3 is a western blot assay detecting expression of DsRed2 protein by the recombinant Rispens/rpsLneo-DsRed2 viruses.

As shown in FIG. 3, protein bands of 26 kilodaltons (kDa), which was the expected size of the DsRed2 protein, was observed only in the lanes with the recombinant virus infected cells.

Example 6: Growth Kinetics and Plaque Morphology of Recombinant Rispens/rpsLneo-DsRed2

Growth kinetics and plaque morphology of recombinant Rispens/rpsLneo-DsRed2 and parent Rispens were compared. Briefly, $9.5 \times 10^5$ cells of CEF and 950 plaque forming unit of one of the recombinant Rispens/rpsLneo-DsRed2 viruses or the parent Rispens strain were planted into 6-well plates. Cells were harvested at 0, 24, 48, 72, 96, 120, or 144 hour. The cells were trypsinized and resuspended in 1 ml of LM medium, and titrated immediately by plaque assay. For plaque assay, CEF cells were infected with serial tenfold dilutions of trypsinized cells. Four days later, plaques were visualized by black plaque assay. Briefly, the cells were fixed with methanol:acetone mixture (1:2) and incubated with anti-Rispens monoclonal antibody 2BN90 (AVIAN DISEASES 37: 561-567, 1993). Next, incubated with biotinylated anti-mouse IgG antibody and then with VECTASTAIN ABC-AP kit, Rispens plaques were stained by addition of NBT/BCIP solution. The numbers of the plaques were counted macroscopically and the average size of fifty plaques was calculated using the program cellSens standard (OLYMPUS) for plaque morphology.

Figure 4:
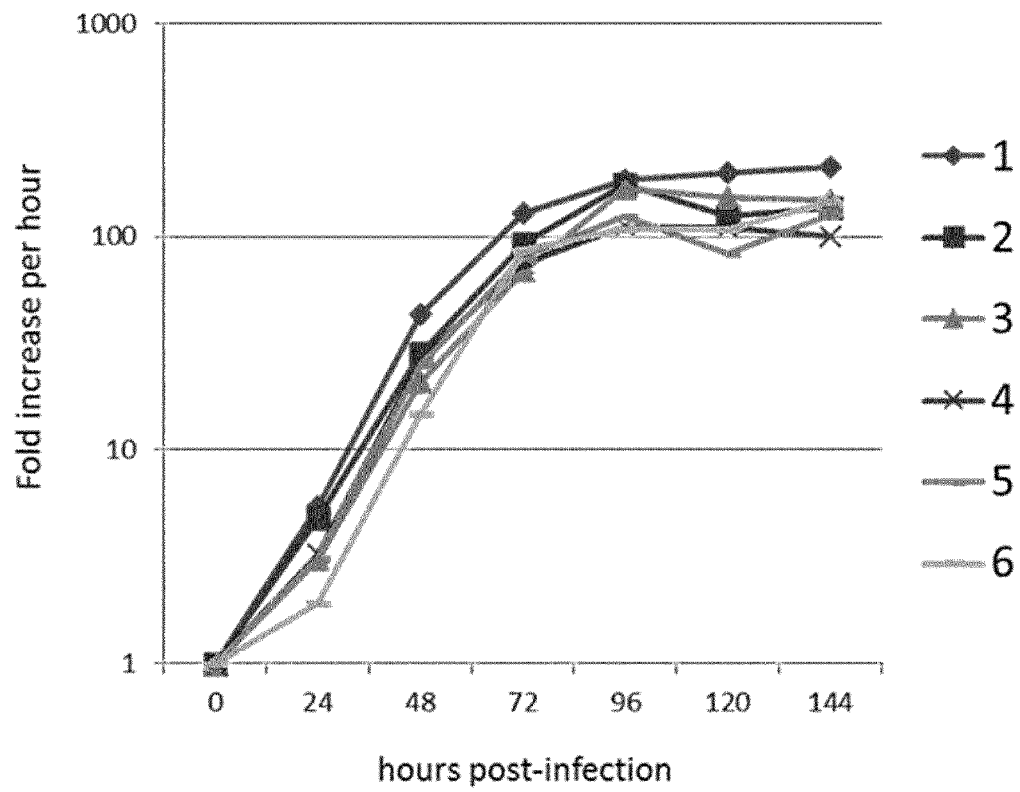
FIG. 4 illustrates growth kinetics of recombinant Rispens/rpsLneo-DsRed2 or parental Rispens.
Figure 5:
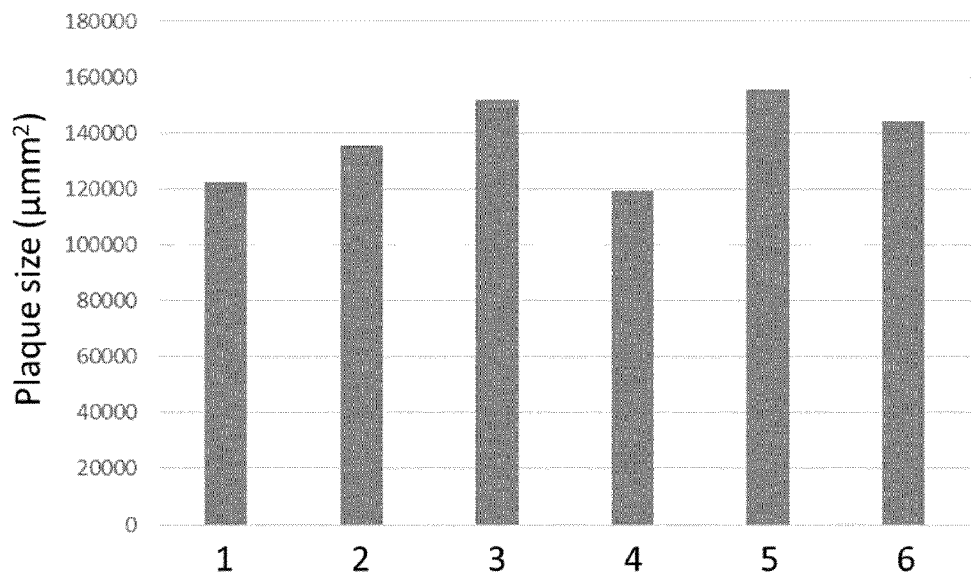
FIG. 5 illustrates average plaque size of recombinant Rispens/rpsLneo-DsRed2 or parental Rispens.

As shown in FIGS. 4 and 5, all recombinant Rispens/rpsLneo-DsRed2 viruses of the invention grew comparably to parental Rispens.

Example 7: In Vitro Stability Analysis of Recombinant Rispens/rpsLneo-DsRed2

In vitro stability of recombinant Rispens/rpsLneo-DsRed2 was analysed using CEF cells. Briefly, CEF cells in 6-well plates were infected with one of the recombinant Rispens/rpsLneo-DsRed2 viruses at a multiplicity of infection of approximately 0.001. Three to four days after infection, infected cells were trypsinized and transferred to new 6-well plates with CEF cells. The infected cells were passed fifteen times, and genome structures and DsRed2 expression were confirmed every five passages. Genome structures were analysed by PCR amplifying junction regions (Junction 1, Junction 2, and Junction 3; FIG. 2). Primer pairs used were shown in example 4. Expected sizes of PCR products were observed with all of recombinant Rispens/rpsLneo-DsRed2 at all passages. In accord with this result, DsRed2 expression of all the plaques of recombinant Rispens/rpsLneo-DsRed2 at all passages was confirmed by fluorescence microscopy.

Example 8: Construction of Recombinant MDV1 RR043

RR043 is a recombinant MDV1 virus of the invention wherein a VP2 antigen under the control of a synthetic Coa5 promoter is cloned between MDV010 and MDV011 (RR043: Rispens/MDV010/Coa5-VP2stc).

For construction of the virus, a homology vector was first constructed and then used to generate the virus by homologous recombination. Plasmid constructions and DNA manipulation were essentially performed according to standard molecular biology techniques (Molecular Cloning: A Laboratory Manual. 4th Edition, Cold Spring Harbor Laboratory, Cold Spring Harbor, N.Y., USA, 2012).

Construction of pUC18-MDV010-SfiI

Figure 6:
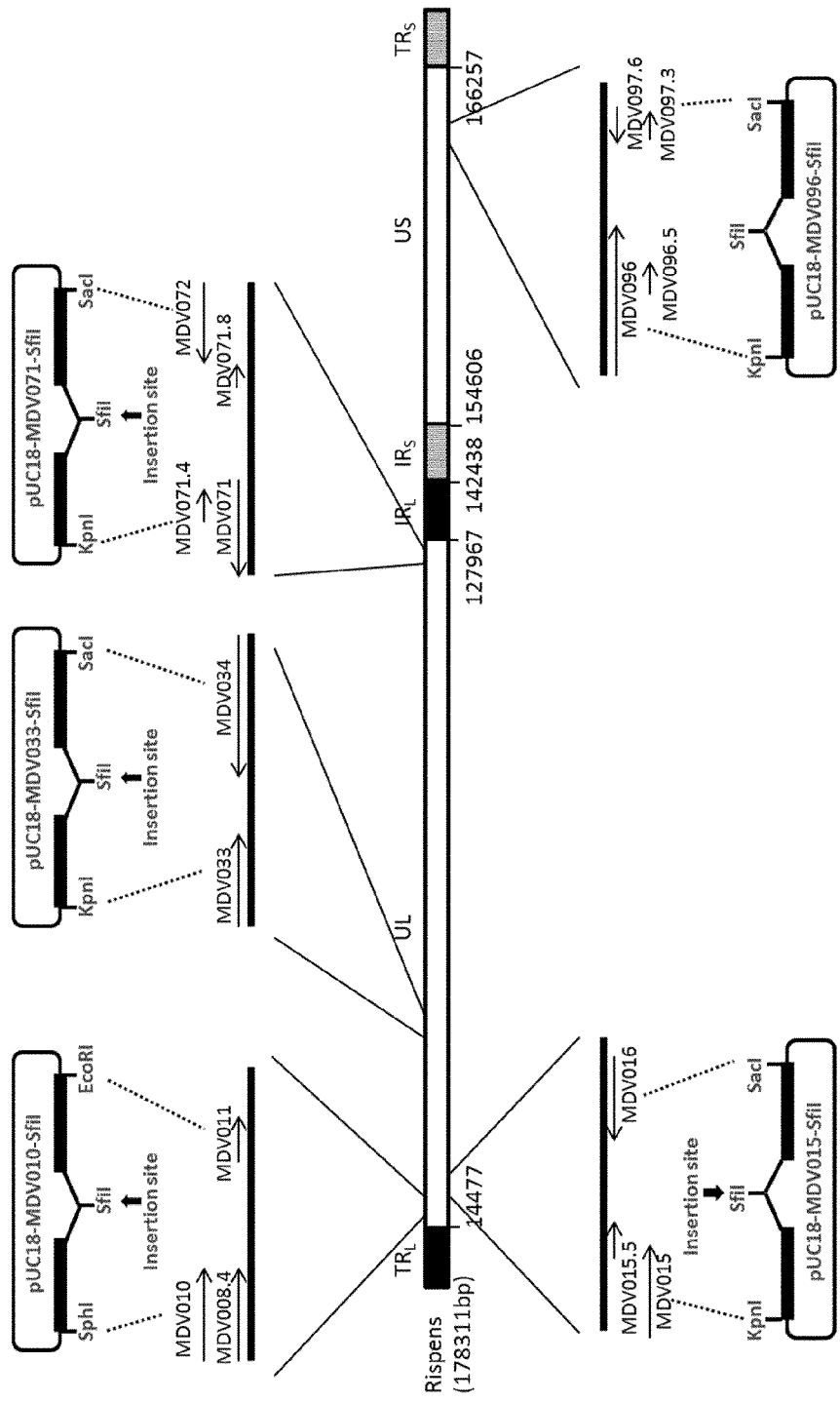
FIG. 6 illustrates a schematic diagram of the Rispens genome and the location of the cloned region of recombinant Rispens/IBD including the insertion site.

A 1.2-kb DNA fragment of Rispens genome flanking the intended insertion site (intergenic region of MDV010/011 containing MDV010 and MDV011 regions) was cloned by PCR reactions adding SfiI recognition site at the insertion site (FIG. 6). Briefly, using DNA extracted from Rispens as a template, two PCR reactions were conducted. Primer pairs used are SEQ ID NO: 29 (5'-GCGCATGCGCACG-CATATAGATCGAAC-3') and SEQ ID NO: 30 (5'-CGGC-CAATAAGGCCCCCAATGTTATAATTA-3'), and SEQ ID NO: 31 (5'-GCGAATTCATAACAGAATGTCACGA-TAAAG-3') and SEQ ID NO: 32 (5'-GGGCCTTATTGGC-CGAATGTATTTAACAGC-3'). Another PCR reaction was conducted using a mixture of PCR products from the two previous PCR reactions as a template and SEQ ID NO: 29 and SEQ ID NO: 31 as primers. An obtained PCR fragment was cloned into pUC18 vector (GenBank Acc. No. L09136) after digestion with EcoRI and SphI, resulting in pUC18-MDV010-SfiI.

Construction of the Homology Vector

Utilizing plasmid pUC18-MDV010-SfiI, a homology vector containing a promoter and IBDV VP2 gene from standard challenge strain (VP2-STC) was constructed. In this experiment, homology plasmid containing a partial core sequence (SEQ ID NO: 33) of Bac promoter (Coa5 promoter) was constructed. First, pUC18-MDV010-SfiI was cleaved with SfiI and dephosphorylated with Alkaline Phosphatase *Shewanella* sp. S1B1 Recombinant (PAP) (Funakoshi #DE110). The Coa5 promoter was obtained from the plasmid pGICOA (U.S. Pat. No. 6,866,852) by BglI and XbaI digestion, and ligated with a XbaI-EcoRI fragment (6.3-kb) and an EcoRI-BglI fragment (0.1-kb) of p45/46bacVP2-STC#11 (U.S. Pat. No. 6,764,684), resulting in p45/46COA5VP2-STC#11. The Coa5 promoter-VP2-STC cassette was then cut out from p45/46COA5VP2-STC#11 by Bgl1 digestion and ligated with the SfiI-digested pUC18-MDV010-SfiI, resulting in pUC18-MDV010-Coa5VP2stc. This plasmid was used to construct RR043.

Construction of Recombinant RR043

Construction of RR043 was conducted by homologous recombination. In a first production experiment, viral DNA of wild type Rispens virus was prepared as described by Morgan et al. (Avian Diseases, 34:345-351, 1990). Approximately 2 μg of the Rispens DNA and 1 μg of the homology plasmid were transfected into approximately $10^7$ CEF cells by electroporation using Nucleofector II (Lonza, Basel, Switzerland). The transfected cells were added to LM (+) medium, planted in 96-well tissue culture plates, and then incubated at 37° C. in 4-5% $CO_2$ for 5-7 days until Rispens plaques became visible. The cells were then detached from the plates by trypsinization, transferred equally to two 96-well plates with CEF, and incubated for 4 to 6 days until plaques were observed. Screening was conducted by the black plaque assay, staining only plaques expressing IBDV VP2 protein. Briefly, one of the two plates was fixed with methanol:acetone mixture (1:2) and incubated with anti-IBDV VP2 monoclonal antibody R63 (ATCC #: HB-9490). Next, incubated with biotinylated anti-mouse IgG antibody (Vector Laboratories, Cat#BA-9200) and then with VECTASTAIN ABC-AP kit (Vector Laboratories, Cat#AK-5000), plaques expressing VP2 protein were stained by addition of NBT/BCIP solution (Roche Applied Science, Cat#1681451). Wells containing stained recombinant plaques were identified and cells from the corresponding wells on the other 96-well plate were trypsinized. The cells were then diluted in fresh secondary CEF cells and transferred to 96-well plates to complete the first round of purification. The purification procedure was repeated until all plaques were stained positively in the black plaque assay.

In another production experiment, DH10B *E. coli* strain carrying Rispens genome as BAC is transfected with 1 μg of the homology vector. Transfection is conducted by electroporation using Gene Pulser Xcell at 1.75 kV, 25 μF, and 200 ohm. After transfection, the *E. coli* is plated onto LB agar plates, and incubated overnight at 37° C. *E. coli* clones carrying an appropriate insert containing the VP2 gene are identified by PCR using a primer pair amplifying a region between VP2 gene and the insertion site region of Rispens genome. The primers are SEQ ID NO: 34 (5'-GAGCAACT-TCGAGCTGATCC-3') and SEQ ID NO: 24. Rispens BAC DNA is extracted from clones that contained the insert and transfected into CEF using Nucleofector II. The transfected CEF are planted in 96-well plates and incubated at 37° C. in 4-5% $CO_2$ for 5-7 days until Rispens plaques become visible. Plaques expressing VP2 protein are purified as described above.

Example 9: Construction of Recombinant MDV1 RR044

RR044 is a recombinant MDV1 virus of the invention wherein a VP2 antigen under the control of a synthetic Coa5 promoter is cloned between MDV015 and MDV016 (RR044: Rispens/MDV015/Coa5-VP2stc).

For construction of the virus, a homology vector was first constructed and then used to generate the virus by homologous recombination. Plasmid constructions and DNA manipulation were essentially performed according to standard molecular biology techniques (Molecular Cloning: A Laboratory Manual. 4th Edition, Cold Spring Harbor Laboratory, Cold Spring Harbor, N.Y., USA, 2012).

Construction of pUC18-MDV015-SfiI

A 1.2-kb DNA fragment of Rispens genome flanking the intended insertion site (intergenic region of MDV015/016 containing MDV015 and MDV016 regions) was cloned by PCR reactions adding SfiI recognition site at the insertion site (FIG. 6). Briefly, using DNA extracted from Rispens as a template, two PCR reactions were conducted. Primer pairs used are SEQ ID NO: 35 (5'-GCGGTACCGCCCTA-GAACTCAGCCGAGT-3') and SEQ ID NO: 36 (5'-AGGC-CAATAAGGCCGTAATAAAACACATCT-3'), and SEQ ID NO: 37 (5'-GCGAGCTCCGTCTTAACTATTATGTG-GATG-3') and SEQ ID NO: 38 (5'-CGGCCTTATTGGCCT-TGCCTTTTACAGGGG-3'). Another PCR reaction was conducted using a mixture of PCR products from the two previous PCR reactions as a template and SEQ ID NO: 35 and SEQ ID NO: 37 as primers. An obtained PCR fragment was cloned into pUC18 vector (GenBank Acc. No. L09136) after digestion with KpnI and SacI, resulting in pUC18-MDV015-SfiI.

Construction of the Homology Vector

Utilizing plasmid pUC18-MDV015-SfiI, a homology vector containing a promoter and IBDV VP2 gene from standard challenge strain (VP2-STC) was constructed. In this experiment, homology plasmid containing a partial core sequence (SEQ ID NO: 33) of Bac promoter (Coa5 promoter) was constructed. First, pUC18-MDV015-SfiI was cleaved with SfiI and dephosphorylated with Alkaline Phosphatase Shewanella sp. S1B1 Recombinant (PAP) (Funakoshi #DE110). Then, the Coa5 promoter-VP2-STC cassette was cut out from p45/46COA5VP2-STC#11 by BglI digestion and ligated with the SfiI-digested pUC18-MDV015-SfiI, resulting in pUC18-MDV015-Coa5VP2stc. This plasmid was used to construct RR044.

Construction of Recombinant RR044

Construction of recombinant RR044 is conducted by homologous recombination, as described in Example 8. RR044 clones carrying an appropriate insert containing the VP2 gene can be identified by PCR using a primer pair amplifying a region between VP2 gene and the insertion site region of Rispens genome, e.g., SEQ ID NO: 34 and SEQ ID NO: 25.

Example 10: Construction of Recombinant MDV1 RR045

RR045 is a recombinant MDV1 virus of the invention wherein a VP2 antigen under the control of a synthetic Coa5 promoter is cloned between MDV033 and MDV034 (RR045: Rispens/MDV033/Coa5-VP2stc).

For construction of the virus, a homology vector was first constructed and then used to generate the virus by homologous recombination. Plasmid constructions and DNA manipulation were essentially performed according to standard molecular biology techniques (Molecular Cloning: A Laboratory Manual. 4th Edition, Cold Spring Harbor Laboratory, Cold Spring Harbor, N.Y., USA, 2012).

Construction of pUC18-MDV033-SfiI

A 1.2-kb DNA fragment of Rispens genome flanking the intended insertion site (intergenic region of MDV033/034 containing MDV033 and MDV034 regions) was cloned by PCR reactions adding SfiI recognition site at the insertion site (FIG. 6). Briefly, using DNA extracted from Rispens as a template, two PCR reactions were conducted. Primer pairs used are SEQ ID NO: 39 (5'-GCGGTACCTTCGCGAGT-TGTGCGATCATC-3') and SEQ ID NO: 40 (5'-AGGC-CAATAAGGCCGAATTTATTTCGCGTG-3'), and SEQ ID NO: 41 (5'-GCGAGCTCTTTGCCCATTTCTG-GACTAGG-3') and SEQ ID NO: 42 (5'-CGGCCTTATTG-GCCTATACATAGCTTGTTA-3'). Another PCR reaction was conducted using a mixture of PCR products from the two previous PCR reactions as a template and SEQ ID NO: 39 and SEQ ID NO: 41 as primers. An obtained PCR fragment was cloned into pUC18 vector (GenBank Acc. No. L09136) after digestion with KpnI and SacI, resulting in pUC18-MDV033-SfiI.

Construction of the Homology Vector

Utilizing plasmid pUC18-MDV033-SfiI, a homology vector containing a promoter and IBDV VP2 gene from standard challenge strain (VP2-STC) was constructed. In this experiment, homology plasmid containing a partial core sequence (SEQ ID NO: 33) of Bac promoter (Coa5 promoter) was constructed. First, pUC18-MDV033-SfiI was cleaved with SfiI and dephosphorylated with Alkaline Phosphatase Shewanella sp. S1B1 Recombinant (PAP) (Funakoshi #DE110). Then, the Coa5 promoter-VP2-STC cassette was cut out from p45/46COA5VP2-STC#11 by BglI digestion and ligated with the SfiI-digested pUC18-MDV033-SfiI, resulting in pUC18-MDV033-Coa5VP2stc. This plasmid was used to construct RR045.

Construction of Recombinant RR045

Construction of recombinant RR045 is conducted by homologous recombination, as described in Example 8. RR045 clones carrying an appropriate insert containing the VP2 gene can be identified by PCR using a primer pair amplifying a region between VP2 gene and the insertion site region of Rispens genome, e.g., SEQ ID NO: 34 and SEQ ID NO: 26.

Example 11: Construction of Recombinant MDV1 RR046

RR046 is a recombinant MDV1 virus of the invention wherein a VP2 antigen under the control of a synthetic Coa5 promoter is cloned between MDV071 and MDV072 (RR046: Rispens/MDV071/Coa5-VP2stc).

For construction of the virus, a homology vector was first constructed and then used to generate the virus by homologous recombination. Plasmid constructions and DNA manipulation were essentially performed according to standard molecular biology techniques (Molecular Cloning: A Laboratory Manual. 4th Edition, Cold Spring Harbor Laboratory, Cold Spring Harbor, N.Y., USA, 2012).

Construction of pUC18-MDV071-SfiI

A 1.2-kb DNA fragment of Rispens genome flanking the intended insertion site (intergenic region of MDV071/072 containing MDV071 and MDV072 regions) was cloned by PCR reactions adding SfiI recognition site at the insertion site (FIG. 6). Briefly, using DNA extracted from Rispens as a template, two PCR reactions were conducted. Primer pairs used are SEQ ID NO: 43 (5'-GCGGTACCTCCATATAT-GTTTCCGTCCTG-3') and SEQ ID NO: 44 (5'-TGGC-CAATAAGGCCTCCATTATGTGATTGC-3'), and SEQ ID NO: 45 (5'-GCGAGCTCATAACTGCAGAAAC-CAAACG-3') and SEQ ID NO: 46 (5'-AGGCCTTATTG- GCCATCAAAGGCCTCAAAG-3'). Another PCR reaction was conducted using a mixture of PCR products from the two previous PCR reactions as a template and SEQ ID NO: 43 and SEQ ID NO: 45 as primers. An obtained PCR fragment was cloned into pUC18 vector (GenBank Acc. No. L09136) after digestion with KpnI and SacI, resulting in pUC18-MDV071-SfiI.

Construction of the Homology Vector

Utilizing plasmid pUC18-MDV071-SfiI, a homology vector containing a promoter and IBDV VP2 gene from standard challenge strain (VP2-STC) was constructed. In this experiment, homology plasmid containing a partial core sequence (SEQ ID NO: 33) of Bac promoter (Coa5 promoter) was constructed. First, pUC18-MDV071-SfiI was cleaved with SfiI and dephosphorylated with Alkaline Phosphatase *Shewanella* sp. S1B1 Recombinant (PAP) (Funakoshi #DE110). Then, the Coa5 promoter-VP2-STC cassette was cut out from p45/46COA5VP2-STC#11 by BglI digestion and ligated with the SfiI-digested pUC18-MDV071-SfiI, resulting in pUC18-MDV071-Coa5VP2stc. This plasmid was used to construct RR046.

Construction of Recombinant RR046

Construction of recombinant RR046 is conducted by homologous recombination, as described in Example 8. RR046 clones carrying an appropriate insert containing the VP2 gene can be identified by PCR using a primer pair amplifying a region between VP2 gene and the insertion site region of Rispens genome, e.g., SEQ ID NO: 34 and SEQ ID NO: 27.

Example 12: Construction of Recombinant MDV1 RR047

RR047 is a recombinant MDV1 virus of the invention wherein a VP2 antigen under the control of a synthetic Coa5 promoter is cloned between MDV096 and MDV097.6 (RR047: Rispens/MDV096/Coa5-VP2stc).

For construction of the virus, a homology vector was first constructed and then used to generate the virus by homologous recombination. Plasmid constructions and DNA manipulation were essentially performed according to standard molecular biology techniques (Molecular Cloning: A Laboratory Manual. 4th Edition, Cold Spring Harbor Laboratory, Cold Spring Harbor, N.Y., USA, 2012).

Construction of pUC18-MDV096-SfiI

A 1.1-kb DNA fragment of Rispens genome flanking the intended insertion site (intergenic region of MDV096/097.6 containing MDV096 and MDV097.6 regions) was cloned by PCR reactions adding SfiI recognition site at the insertion site (FIG. 6). Briefly, using DNA extracted from Rispens as a template, two PCR reactions were conducted. Primer pairs used are SEQ ID NO: 47 (5'-GCGGTACCTTTTACTCA-CATCGCTATC-3') and SEQ ID NO: 48 (5'-AGGC-CAATAAGGCCTGTTGCAGTGGTGCTA-3'), and SEQ ID NO: 49 (5'-GCGAGCTCGCTGCATATTGCATCAC-TATA-3') and SEQ ID NO: 50 (5'-AGGCCTTATTGGCCT-GTGGTTTATCGATTT-3'). Another PCR reaction was conducted using a mixture of PCR products from the two previous PCR reactions as a template and SEQ ID NO: 47 and SEQ ID NO: 49 as primers. An obtained PCR fragment was cloned into pUC18 vector (GenBank Acc. No. L09136) after digestion with KpnI and SacI, resulting in pUC18-MDV096-SfiI.

Construction of the Homology Vector

Utilizing plasmid pUC18-MDV096-SfiI, a homology vector containing a promoter and IBDV VP2 gene from standard challenge strain (VP2-STC) was constructed. In this experiment, homology plasmid containing a partial core sequence (SEQ ID NO: 33) of Bac promoter (Coa5 promoter) was constructed. First, pUC18-MDV096-SfiI was cleaved with SfiI and dephosphorylated with Alkaline Phosphatase *Shewanella* sp. S1B1 Recombinant (PAP) (Funakoshi #DE110). Then, the Coa5 promoter-VP2-STC cassette was cut out from p45/46COA5VP2-STC#11 by BglI digestion and ligated with the SfiI-digested pUC18-MDV096-SfiI, resulting in pUC18-MDV096-Coa5VP2stc. This plasmid was used to construct RR047.

Construction of Recombinant RR047

Construction of recombinant RR047 is conducted by homologous recombination, as described in Example 8. RR047 clones carrying an appropriate insert containing the VP2 gene can be identified by PCR using a primer pair amplifying a region between VP2 gene and the insertion site region of Rispens genome, e.g., SEQ ID NO: 34 and SEQ ID NO: 28.

Example 13: Verification of Genome Structure

Figure 7:
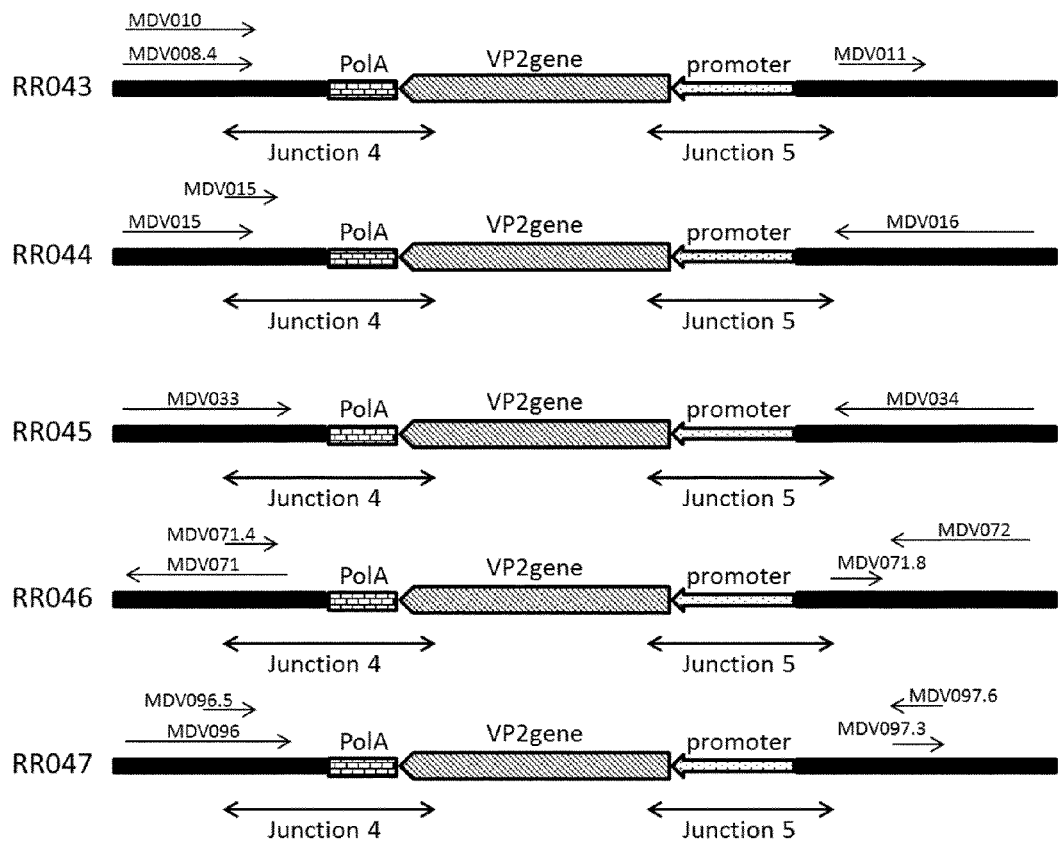
FIG. 7 shows a diagram of recombinant Rispens/IBD genome, indicating locations of Junction 4 and Junction 5 amplified in PCR reactions to confirm the genome structures of the viruses.

Genome structures of the recombinant Rispens/IBD were verified by two PCR reactions amplifying junction regions (Junction 4 and Junction 5) at each end of the inserted genes. FIG. 7 shows where Junction 4 and Junction 5 are located in the recombinant virus genome. For junction 4, the primer pairs used in the PCR reactions are SEQ ID NO: 34 and SEQ ID NO: 24 for RR043, SEQ ID NO: 25 for RR044, SEQ ID NO: 26 for RR045, SEQ ID NO: 27 for RR046, or SEQ ID NO: 28 for RR047, respectively. For Junction 2, SEQ ID NO: 51 (5'-GCCAGGGAATCCAGGGAAAAAGAC-3') and SEQ ID NO: 18 for RR043, SEQ ID NO: 19 for RR044, SEQ ID NO: 20 for RR045, SEQ ID NO: 21 for RR046, or SEQ ID NO: 22 for RR047, respectively, were used. Expected sizes of PCR products were observed with all of the recombinant Rispens, confirming that these recombinant Rispens have the expected genome structures.

Example 14: Expression of an Inserted Antigen by Recombinant Rispens

Expression of the VP2 protein by RR043, RR044, RR046, and RR047 was confirmed by the black plaque assay and the Western blot assay. Procedures for the black plaque assay are described in Example 8. The western blot was conducted using CEF cells infected with the recombinant viruses and anti-IBDV VP2 monoclonal antibody R63. Briefly, CEF cells in 6-well plates were infected with one of the recombinant viruses or the parent Rispens strain at a multiplicity of infection of approximately 0.1. Three days post inoculation, cells were harvested with trypsin and centrifuged at 913×g for 5 minutes. The pellet was washed with PBS and resuspended with 100 µl of PBS. After adding the same volume of 2×SDS sample buffer, cell suspension was boiled for 5 minutes. The samples were separated by SDS-PAGE using 12% polyacrylamide gel and transferred to a PVDF membrane (Immobilon-P, Millipore). The membrane was dried completely and then incubated with the R63 monoclonal antibody. After the R63 antibody was washed off, biotinylated anti-mouse IgG antibody (Vector Laboratories, Cat#BA-9200) and then with VECTASTAIN ABC-AP kit (Vector Laboratories, Cat#AK-5000). Protein bound with the R63 monoclonal antibody was visualized by addition of NBT/BCIP solution (Roche Applied Science, Cat#1681451).

Figure 8:
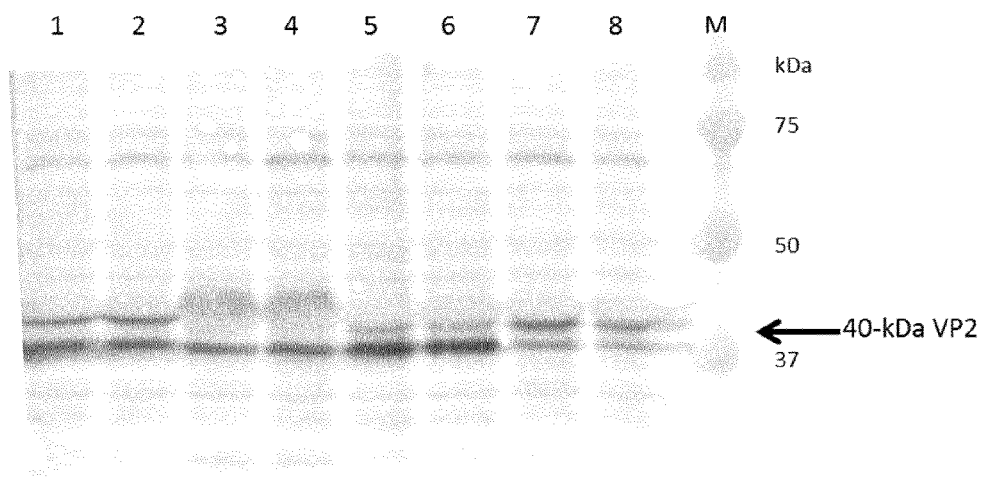
FIG. 8 is a western blot assay detecting expression of IBDV VP2 protein by the recombinant Rispens/IBD viruses.
Figure 9:
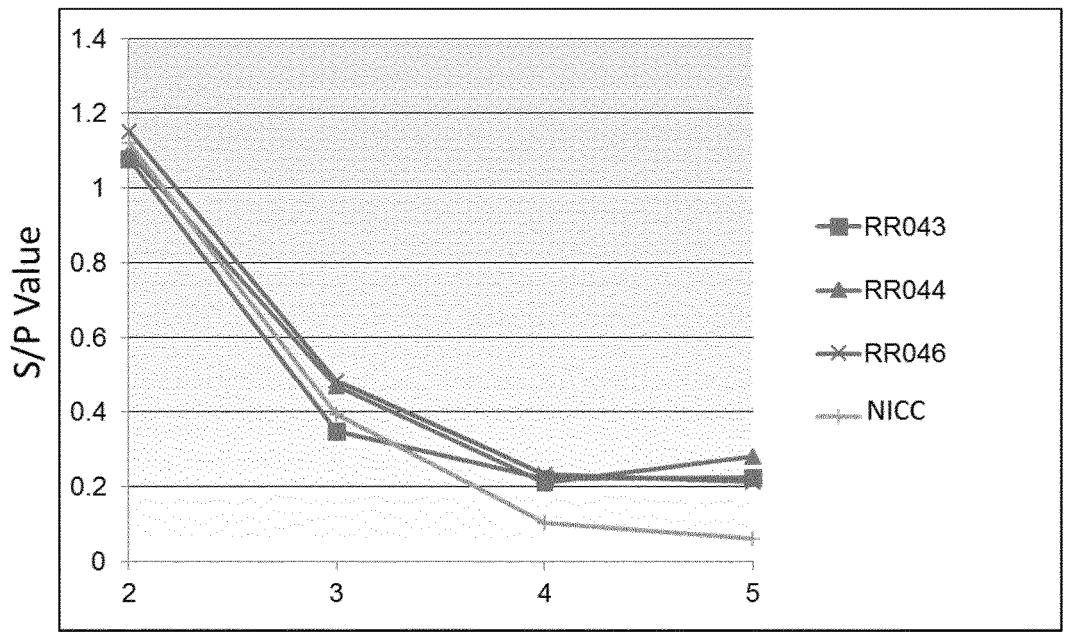
FIG. 9 illustrates IBDV ELISA titers in commercial white leghorn chickens vaccinated with recombinant Rispens/IBD using a commercial IBD ELISA kit.

The results are depicted in FIG. 8. They show that protein bands of 40 kilodaltons (kDa), which is the expected size of the VP2 protein, were observed in all lanes with the recombinant virus infected cells. VP2 protein expression with recombinants RR043 and RR044 is particularly strong, as evidenced by highly marked bands.

Example 15: In Vivo Efficacy of Recombinant Rispens in Chickens

Efficacy of recombinant Rispens viruses of the invention expressing the IBDV VP2 gene was evaluated against virulent IBDV challenge. In this study, three recombinant Rispens/IBD viruses (RR043, RR044, and RR046) were used. Commercial layer (white leghorn) chickens with maternal antibodies at one day of age were divided into five groups and chicks in Groups 3 through 5 were vaccinated subcutaneously with approximately 3000 plaque forming units (pfu)/0.2 ml of one of the recombinant Rispens (Group 3: RR043; Group 4: RR044; Group 5: RR046). Chicks in Group 1 (non-immunized, non-challenged negative control) and chicks in Group 2 (non-immunized, challenged positive control) were left unvaccinated. The chickens were bled each week between 1 and 6 weeks of age for evaluation of humoral immunity against IBDV. Anti-IBDV antibodies were quantitated with a commercial IBDV ELISA kit (Idexx Laboratories, FlockChek IBD). At 5 weeks of age, all chickens except Group 1 were challenged with $10^3$ mean embryo infectious dose ($EID_{50}$) of virulent IBDV standard challenge (STC) strain via oral route. Chickens were observed daily for clinical signs associated with IBD, such as depression and death. Seven days post challenge, chickens were necropsied and observed for grossly observable bursal lesions such as edema, discoloration, atrophy, hemorrhage, and yellow or gelatinous exudates. Weights of body and bursa were also measured at necropsy for calculation of B/B index, which is the ratio between the weight of the bursa and the body weight of challenged birds divided by the same ratio of non-challenged birds.

Table 1 summarizes the results. All chickens in Group 2 (challenged positive control) developed gross bursal lesions typical of IBD, while all chickens in Group 1 (non-challenged negative control) remained free from such lesions. Chickens in all vaccinated Groups show very strong protective immunity, preventing occurrence of disease. Strikingly, protection provided by RR043 (Group 3) was 100% (22/22), which is very remarkable. RR044 and RR046 also showed very high protection level of 90% (Group 4) and 95% (Group 5), respectively. Furthermore, the B/B Index of these groups were 1.03 (RR043), 1.10 (RR044), and 1.01 (RR046), respectively, suggesting no significant atrophy in bursa.

In conclusion, the rMDV1 of the invention provided very strong humoral and protective immunity.

TABLE 1

Protection of recombinant Rispens against virulent IBDV challenge in SPF chickens (Efficacy trial)

| Group number | Group | # chickens | B/B Index | # dead after challenge | # with bursal lesions/# total | % protection |
|---|---|---|---|---|---|---|
| 1 | NINC | 20 | 1.00 | 0 | 0/22 | Not applicable |
| 2 | NICC | 22 | 0.83 | 6 | 22/22 | 0% |
| 3 | RR043 | 22 | 1.03 | 0 | 0/22 | 100% |
| 4 | RR044 | 21 | 1.10 | 0 | 2/21 | 90% |
| 5 | RR046 | 22 | 1.01 | 1 | 1/22 | 95% |

NINC = non-immunized, non-challenged negative controls
NICC = non-immunized, challenged positive controls

The invention claimed is:

1. A recombinant Marek's Disease Virus serotype 1 (rMDV1) comprising a foreign gene in its genome, wherein said foreign gene is located in an untranslated genetic region of the genome, and wherein said untranslated genetic region is located between MDV010 and MDV011, between MDV015.5 and MDV016, between MDV033 and MDV034, between MDV071 and MDV072, or between MDV096 and MDV097.6 of the genome.

2. The rMDV1 of claim 1, wherein the foreign gene is located in an untranslated genetic region located between MDV010 and MDV011, between MDV015.5 and MDV016, or between MDV071 and MDV072.

3. The rMDV1 of claim 1, wherein the foreign gene sequence is inserted in replacement of all or a portion of the untranslated genetic region.

4. The rMDV1 of claim 1, wherein the foreign gene sequence is inserted in the untranslated genetic region without deletion of said untranslated genetic region.

5. The rMDV1 of claim 1, wherein said MDV1 is a Rispens strain of MDV1.

6. The rMDV1 of claim 1, wherein said foreign gene encodes an antigen.

7. The rMDV1 of claim 6, wherein the foreign gene encodes a VP2 antigen of Infectious bursal disease virus (IBDV), a HN antigen of Newcastle disease virus (NDV), a F antigen of NDV, or immunogenic fragments thereof.

8. The rMDV1 of claim 1, wherein the foreign gene is under control of a transcriptional promoter in said genome.

9. The rMDV1 of claim 8, wherein the promoter is selected from the chicken beta-actin (Bac) promoter or a derivative thereof, the Coa5 promoter, the Pec promoter, the Murine Cytomegalovirus (Mcmv) immediate-early (ie)1 promoter, the Human Cytomegalovirus promoter (Hcmv), the Simian virus (SV)40 promoter, and the Rous Sarcoma virus (RSV) promoter, or any fragments thereof which retain a promoter activity.

10. A rMDV1 of claim 1, wherein said rMDV1 comprises a foreign gene encoding VP2 of IBDV positioned into an untranslated region located between MDV010-MDV011, MDV015.5-MDV016, MDV033-MDV034, MDV071-MDV072, or MDV096-MDV097.6 of the genome.

11. A rMDV1 of claim 1, wherein said rMDV1 comprises a foreign gene encoding HN and/or F of NDV positioned into an untranslated region located between MDV010-MDV011, MDV015.5-MDV016, MDV033-MDV034, MDV071-MDV072, or MDV096-MDV097.6 of the genome.

12. A nucleic acid molecule comprising the genome of a rMDV1 of claim 1.

13. A host cell comprising a rMDV1 of claim 1 or a nucleic acid molecule comprising the genome of the rMDV1.

14. A method for producing or replicating a rMDV1 of claim 1, comprising infecting a competent cell with the rMDV1 or a nucleic acid molecule comprising the genome of the rMDV1, and collecting the rMDV1.

15. A composition comprising a rMDV1 of claim 1 and an excipient.

16. A vaccine comprising a rMDV1 of claim 1, an excipient and, optionally, an adjuvant.

17. A rMDV1 of claim 1, for use for immunizing an avian against a pathogen.

18. A vaccination kit for immunizing an avian, which comprises the following components:
   a. an effective amount of a vaccine of claim 16, and
   b. a means for administering said vaccine to said avian.

19. The rMDV1 of claim 6, wherein the antigen is an antigen of an avian pathogen selected from a viral pathogen, a bacterial pathogen, a fungal pathogen, and a protozoa pathogen.

20. The rMDV1 of claim 19, wherein said avian pathogen is selected from Newcastle disease virus (NDV), Gumboro disease virus (Infectious bursal disease virus, IBDV), infectious laryngotracheitis virus (ILTV), infectious bronchitis-virus (IBV), *mycoplasma* (MG), or coccidia.

* * * * *